US012558322B2

(12) United States Patent
Lee

(10) Patent No.: US 12,558,322 B2
(45) Date of Patent: Feb. 24, 2026

(54) CONTROL METHOD OF LOCAL RELEASE FOR TARGET COMPOUNDS BY USING PATTERNING HYDROGEL TO NANOPOROUS MEMBRANE

(71) Applicant: KNU-Industry Cooperation Foundation, Gangwon-Do (KR)

(72) Inventor: Kwang Ho Lee, Seoul (KR)

(73) Assignee: KNU-Industry Cooperation Foundation, Gangwon-do (KR)

( * ) Notice: Subject to any disclaimer, the term of this patent is extended or adjusted under 35 U.S.C. 154(b) by 474 days.

(21) Appl. No.: 18/153,590

(22) Filed: Jan. 12, 2023

(65) Prior Publication Data

US 2023/0172865 A1 Jun. 8, 2023

Related U.S. Application Data

(63) Continuation-in-part of application No. 16/453,529, filed on Jun. 26, 2019, now abandoned.

(30) Foreign Application Priority Data

Jun. 26, 2018 (KR) ........................ 10-2018-0073184

(51) Int. Cl.
| | |
|---|---|
| *A61K 9/48* | (2006.01) |
| *A61K 9/20* | (2006.01) |
| *A61K 9/28* | (2006.01) |
| *A61K 9/70* | (2006.01) |

(52) U.S. Cl.
CPC .......... *A61K 9/4825* (2013.01); *A61K 9/2086* (2013.01); *A61K 9/286* (2013.01); *A61K 9/7007* (2013.01)

(58) Field of Classification Search
None
See application file for complete search history.

(56) References Cited

U.S. PATENT DOCUMENTS

2018/0238780 A1 8/2018 Jeon et al.
2025/0339543 A1* 11/2025 Na ........................... A61P 37/00

FOREIGN PATENT DOCUMENTS

| | | |
|---|---|---|
| KR | 10-2013-0042857 A | 4/2013 |
| WO | WO-2015/199492 A1 | 12/2015 |

OTHER PUBLICATIONS

Yi, M.-H., et al., BioChip J. 14(4): 405 â 420 (2020) (Year: 2020).*
Office Action from corresponding Korean Patent Application No. 10-2018-0073184, dated Feb. 17, 2020.
Khademhosseini, A., et al.; "Micromolding of photocrosslinkable hyaluronic acid for cell encapsulation and entrapment", Journal of Biomedical Materials Research Part A, pp. 522-532, 2006.
Office Action (Non-Final) from corresponding U.S. Appl. No. 16/453,529, dated Dec. 17, 2020.
Office Action (Final) from corresponding U.S. Appl. No. 16/453,529, dated Jun. 15, 2021.
Office Action (Non-Final) from corresponding U.S. Appl. No. 16/453,529, dated Dec. 22, 2021.
Office Action (Final) from corresponding U.S. Appl. No. 16/453,529, dated Aug. 16, 2022.
Lee, K., et al.; Lab Chip 11: 1168-1173 (2011).
Jeon, O., et al., Small 14: 1800579 (May 21, 2018). (Year: 2018).
Kan, S., et al., 18th International Conference on Miniaturized Systems for Chemistry and Life Sciences, pp. 1734-1736 Year: 2014).
Holister, P., et al., Nanoporous Materials (2003). (Year: 2003).
Mager, M. and N. Melosh, Adv. Mater. 20: 4423-4427 (2008). (Year: 2008).
Lee, J.- E.; Lee, S.-M.; Kim, C.-B.; Lee, K.-H. 5-Fluorouracil-Immobilized Hyaluronic AcidHydrogel Arrays on an ElectrospunBilayer Membrane as a Drug Patch.Bioengineering 2022, 9, 742.https://doi.org/10.3390/bioengineering9120742.

* cited by examiner

*Primary Examiner* — David J Blanchard
*Assistant Examiner* — Daniel F Coughlin
(74) *Attorney, Agent, or Firm* — Harness, Dickey & Pierce, P.L.C.

(57) ABSTRACT

Provided is a method of controlling local release of target compounds by patterning a hydrogel carrying a bone morphogenetic protein or anticancer drug as the target compounds onto an electrospun nanoporous membrane. The hydrogel is capable of controlling local release of the bone morphogenetic protein or anticancer drug as a carrier of the bone morphogenetic protein or anticancer. And the electrospun nanoporous membrane performs a basic function of the membrane of preventing infiltration of connective tissue. Thus, there is an advantage in that the hydrogel patterned nanoporous membrane can facilitate generation of controlled bone in a local region and degradation of cancer in a local region.

11 Claims, 15 Drawing Sheets

0 sec.          20 sec.          60sec.          420 sec.

1

CONTROL METHOD OF LOCAL RELEASE FOR TARGET COMPOUNDS BY USING PATTERNING HYDROGEL TO NANOPOROUS MEMBRANE

CROSS-REFERENCE TO RELATED APPLICATION

This application is a continuation-in-part of U.S. patent application Ser. No. 16/453,529, filed on 26 Jun. 2019, which claims benefit of and priority to Korean Patent Application No. 10-2018-0073184, filed on 26 Jun. 2018. The entire disclosure of the applications identified in this paragraph are incorporated herein by reference.

FIELD

The present invention relates to a method of controlling local release of target compounds by patterning a hydrogel onto a nanoporous membrane.

BACKGROUND

This work was supported by a grant from the Basic Science Research Program (2021R1F1A1063781), Regional Innovation Strategy (2022RIS-005), "Leaders in INdustry-university Cooperation 3.0" Project through the National Research Foundation of Korea (NRF) and the Ministry of Education (MOE), and Universities leading lab-specific start-ups through the Commercializations Promotion Agency for R&D Outcomes (COMPA) by the Korea government (MSIT) (No. STARTUPLAB22-011).

In the field of dentistry and orthopedics in the related art, for formation and reconstruction of a bone tissue which has been damaged, bone morphogenetic proteins have been used. These materials can only be used for regeneration and treatment of the damaged tissue if the materials are released locally in a human body. However, in the current techniques, there have been used methods of synthesizing carriers or nanoparticles in a drug in a polymeric-based fibrous membrane and attaching the carriers or nanoparticles or immobilizing attaching the carriers or nanoparticles by injection to a desired tissue region. However, because the growth of bone may be induced in an undesired tissue region and delivery of the drug is not quantitative, the technique has difficulties in correct treatment for bone formation.

The following Table 1 lists the types of bone morphogenetic proteins used for the regeneration of damaged bone.

TABLE 1

Knockout phenotypes and biological consequences for the major players in BMP signaling.

| Signaling molecule | Phenotype |
|---|---|
| BMP1 | Die after birth, failure of ventral body wall closure |
| BMP2 | Embryonically lethal, defects in amnion/chorion and cardiac development; limb: spontaneous fractures and impaired fracture repair; chondrocyte: severe chondrodysplasia; cardiac progenitor: abnormal heart valve development; myocardium: defects in myocardial patterning |
| BMP3 | Increased bone density |
| BMP4 | Embryonically lethal, lack of mesoderm formation, no PGCs, no lens induction; heterozygotes: various organ abnormalities; hypomorph: AVCD, HSC microenvironment defect; limb bud mesoderm: defective digit patterning; adipocyte: enlarged adipocytes and impaired insulin sensitivity'; other targeted: loss-of-trachea phenotype, abnormal branchial arch arteries and outflow tract septation, defects in mandibular development, defects in vestibular apparatus |
| BMP5 | Short ear phenotype; smaller and weaker bones |
| BMP6 | Delay in sternum ossification; smaller long bones; decreased fertility |
| BMP7 | Die after birth, defects in kidney and eye development; defects in skeletal patterning; impaired corticogenesis; decreased brown fat, diminished Langerhans cell number; inducible deletion: precocious differentiation of kidney progenitor cells; limb: no effect; podocyte: defective kidney development |
| BMP8 | Germ cell degeneration; defective PGC formation; germ cell deficiency and infertility |
| BMP9/GDF2 | Abnormal lymphatic development |
| BMP10 | Reduced cardiomyocyte proliferation |
| BMP11/GDF11 | Die after birth, defects in A-P patterning; smaller pancreas; reduced-cell numbers; kidney agenesis; slower spinal cord neuron differentiation; increased olfactory neurogenesis; retinal abnormalities |
| BMP12/GDF7 | Increased endochondral bone growth'; smaller bone cross-sectional parameters; no effect on tail tendon phenotype; subtle effects on Achilles tendon; defective dorsal interneuron formation; sterile with seminal vesicle defects |
| BMP13/GDF6 | Bone fusions in wrists and ankles; accelerated coronal suture fusion; eye and neural defects; Ktippel-Feil syndrome; mates: lower tail tendon collagen |
| BMP14/GDF5 | Brachypodism; malformations in bones of limb, sternum, and digits; delayed fracture healing; impaired joint formation and osteoarthritis; weaker Achilles tendon; increased scarring after myocardial infarction; altered skin properties |
| BMP15 | Males: normal and fertile; females: subfertile with decreased fertilization and ovulation rates |

In addition, in order to regenerate the damaged bone, it is necessary to use a membrane to prevent the formation of scar tissue by blocking a connective tissue from infiltrating into the damaged region for a certain period of time. However, in the techniques, only the blocking of infiltration of the connective tissue into an existing membrane is is performed (in FIG. 1, a schematic diagram of a restoration process and a membrane for regenerating a bone is illustrated).

Cancer, one of the leading causes of death worldwide, is a disease wherein abnormal cells grow uncontrollably and form a mass called tumor. Tumor cells can sometimes migrate to surrounding host tissues through blood circulation or lymph nodes; this process is commonly referred to as metastasis. The main treatments of cancer are surgery, radiation therapy, and chemotherapy. In brief, surgery is a common treatment for many types of cancer, wherein the tumor mass and some of the nearby tissues are excised. Radiation therapy uses high energy beams to destroy cancer cells and shrink tumors. Chemotherapy is a systemic treatment that uses anticancer drugs to prevent or kill cancer cells based on injections and orally administered pills. Usually, anticancer drugs introduced into the body are transported through blood vessels and circulate throughout the body to prevent the growth of or kill cancer cells. Despite the convenience of use and high effectiveness, most anticancer drugs are cytotoxic and kill cancer cells (that rapidly divide) by blocking division; however, this leads to side effects that damage normal cells. Molecular targeted therapies are becoming a preferred alternative in that they can minimize the side effects of anticancer drugs; however, personalized medicine (targeting individual patients) has a high cost. Recently, to increase the effects of a drug and minimize side effects according to a patient's disease or physical characteristics, drug delivery systems have been proposed to efficiently deliver a drug to a target site.

It is an essential technology used to selectively deliver a drug according to the site of the disease, or to release the drug periodically, while controlling the released amount. However, the effectiveness of these systems is still not satisfactory for clinical applications. Several studies have been conducted to create micro- or nanosized ultrafine structures based on micro- and nanotechnologies, and deliver cancer-killing drugs to cancer cells. Numerous drug delivery carriers have been developed, including polymers, nanolipids, and inorganic substances; however, the drug-encapsulated carrier is small and has a low renal clearance, which results in its rapid excretion through blood circulation. In addition, tumor microvessels with high interstitial fluid pressure have high intratumoral drug penetration rate, thereby reducing the therapeutic effect of the drug. Hydrogels, which have been attracting attention recently, are being used for continuous administration of hydrophilic and hydrophobic biomolecules, with a high-drug loading dose, regardless of the microvascular system of the tumor; accordingly, controlled release of the drug has become possible by controlling the fiber concentration. In particular, when a hydrogel and multiple drugs are administered in combination, the anticancer effect of the drug increases and drug tolerance decreases. Whenever strong anticancer drugs are developed, their effective delivery to the cancer cell site with minimal side effects is always a challenge.

Therefore, in the present invention, the delivery of the bone morphogenetic protein and anticancer drug using hydrogel and the function of the membrane are simultaneously performed.

REFERENCES

1. Yamamoto, M., Hokugo, A., Takahashi, Y., Nakano, T., Hiraoka, M. & Tabata, Y. Combination of BMP2-releasing gelatin/beta-TCP sponges with autologous bone marrow for bone regeneration of X-ray irradiated rabbit ulnar defects. Biomaterials 56, 18-25 (2015).
2. Wang, C. K., Ho, M. L., Wang, G. J., Chang, J. K., Chen, C. H., Fu, Y. C. & Fu, H. H. Controlled-release of rhBMP-2 carriers in the regeneration of osteonecrotic bone. Biomaterials 30, 4178-4186 (2009).
3. Santo, V. E., Duarte, A. R., Popa, E. G., Gomes, ME., Mano, J. F. & Reis, R. L. Enhancement of osteogenic differentiation of human adipose derived stem cells by the controlled release of platelet lysates from hybrid scaffolds produced by super critical fluid foaming. J. Controlled Release 162, 19-27 (2012).
4. Lee, S. S., Hsu, E. L., Mendoza, M., Ghodasra, J., Nickoli, M. S., Ashtekar, A., Polavarapu, M., Babu, J., Riaz, R. M., Nicolas, J. D., Nelson, D., Hashmi, S. Z., Kaltz, S. R., Earhart, J. S., Merk, B. R., McKee, J. S., Bairstow, S. F., Shah, R. N., Hsu, W. K. & Stupp, S. I. Gel scaffolds of BMP-2-binding peptide amphiphile nanofibers for spinal arthrodesis. Adv. Healthcare Mater. 4, 131-141 (2015).
5. Yao, Q., Liu, Y., Selvaratnam, B., Koodali, R. T. & Sun, H. Mesoporous silicate nanoparticles/3D nanofibrous scaffold-mediated dual-drug delivery for bone tissue engineering. J. Controlled Release 279, 69-78 (2018).
6. Tuncaboylu, D. C., Friess, F., Wischke, C. & Lendlein, A. A multifunctional multimaterial system for on-demand protein release. J. Controlled Release 284, 240-247 (2018).
7. Oliveira, H. F. D., Weiner, A. A., Majumder, A. & Shastri, V. P. Non-covalent surface engineering of an alloplastic polymeric bone graft material for controlled protein release. J. Controlled Release 126, 237-245 (2008).
8. Dumas, A., Moreau, M. F., Gherardi, R. K., Basle, M. F. & Chappard, D. Bone grafts cultured with bone marrow stromal cells for the repair of critical bone defects: an experimental study in mice. J. Biomed. Mater. Res., Part A 90, 1218-1229 (2009).
9. Jia, W. T., Lau, G. Y., Huang, W. H., Zhang, C. Q., Tomsia, A. P. & Fu, Q. Bioactive glass for large bone repair. Adv. Healthcare Mater. 4, 2842-2848 (2015).
10. Checchi, M., Bertacchini, J., Grisendi, G., Smargiassi, A., Sola, A., Messori, M. & Palumbo, C. Proposal of a novel natural biomaterial, the scleral ossicle, for the development of vascularized bone tissue in vitro. Biomedicines 6, (2017).
11. Datta, P. Dhawan, A., Yu, Y., Hayes, D., Gudapati, H. & Ozbolat, I. T. Bioprinting of osteochondral tissues: A perspective on current gaps and future trends. Int. J. Bioprint. 3, 109-120 (2017).
12. Dimitriou, R., Jones, E., McGonagle, D. & Giannoudis, P. V. Bone regeneration: current concepts and future directions. BMC Med. 9, 66 (2011).
13. Maroulakos, M., Kamperos, G., Tayebi, L., Halazonetis, D. & Ren, Y. J. Applications of 3D printing on craniofacial bone repair: A systematic review. J. Dent. 80, 1-14 (2019).
14. Santos, D., Silva, D. M., Gomes, P. S., Fernandes, M. H., Santos, J. D. & Sencadas, V. Multifunctional PLLA-ceramic fiber membranes for bone regeneration applications. J. Colloid Interface Sci. 504, 101-110 (2017).
15. Agrawal, V. & Sinha, M. A review on carrier systems for bone morphogenetic protein-2. J. Biomed. Mater. Res., Part B 105, 904-925 (2017).

16. *Orellana*, B. R., Thomas, M. V., Dziubla, T. D., Shah, N. M., Hilt, J. Z. & Puleo, D. A. Bioerodible calcium sulfate/poly(beta-amino ester) hydrogel composites. J. Mech. Behav. Biomed. Mater. 26, 43-53 (2013).

17. Oryan, A., Alidadi, S., Moshiri, A. & Maffulli, N. Bone regenerative medicine: classic options, novel strategies, and future directions. J. Orthop. Surg. Res. 9, 18 (2014).

18. Weng, L., Boda, S. K., Wang, H., Teusink, M. J., Shuler, F. D. & Xie, J. Novel 3D hybrid nanofiber aerogels coupled with BMP-2 peptides for cranial bone regeneration. Adv. Healthcare Mater. 7, e1701415 (2018).

19. Wozney, J. M. & Rosen, V. Bone morphogenetic protein and bone morphogenetic protein gene family in bone formation and repair. Clin. Orthop. Relat. Res. 346, 26-37 (1998).

20. Chen, B., Lin, H., Wang, J., Zhao, Y., Wang, B., Zhao, W., Sun, W. & Dai, J. Homogeneous osteogenesis and bone regeneration by demineralized bone matrix loading with collagen-targeting bone morphogenetic protein-2. Biomaterials 28, 1027-1035 (2007).

21. Raftery, R. M., Mencia-Castano, I., Sperger, S., Chen, G., Cavanagh, B., Feichtinger, G. A., Redl, H., Hacobian, A. & O'Brien, F. J. Delivery of the improved BMP-2-Advanced plasmid DNA within a gene-activated scaffold accelerates mesenchymal stem cell osteogenesis and critical size defect repair. J. Controlled Release 283, 20-31 (2018).

22. Kim, B. B., Kim, M., Park, Y. H. & Park, J. B. Dexamethasone leads to upregulation of BMP6 and ACHE suppression of SMAD3 and ESR1 genes in human mesenchymal stem cells. Biochip J. 12, 222-230 (2018).

23. Shi, P., Chen, K. & Goh, J. C. Efficacy of BMP-2 delivery from natural protein based polymeric particles. Adv. Healthcare Mater. 2, 934-939 (2013).

24. Kim, S. S., Gwak, S. J. & Kim, B. S. Orthotopic bone formation by implantation of apatite-coated poly(lactide-co-glycolide)/hydroxyapatite composite particulates and bone morphogenetic protein-2. J. Biomed. Mater. Res., Part A 87, 245-253 (2008).

25. Bauer, T. W. & Muschler, G. F. Bone graft materials. An overview of the basic science. Clin. Orthop. Relat. Res. 371, 10-27 (2000).

26. Yu, X., Khalil, A., Dang, P. N., Alsberg, E. & Murphy, W. L. Multilayered inorganic microparticles for tunable dual growth factor delivery. Adv. Funct. Mater. 24, 3082-3093 (2014).

27. Metzger, S. Lienemann, P. S., Ghayor, C., Weber, W., Martin, I., Weber, F. E. & Ehrbar, M. Modular poly (ethylene glycol) matrices for the controlled 3D-localized osteogenic differentiation of mesenchymal stem cells. Adv. Healthcare Mater. 4, 550-558 (2015).

28. Samorezov, J. E., Headley, E. B., Everett, C. R. & Alsberg, E. Sustained presentation of BMP-2 enhances osteogenic differentiation of human adipose derived stem cells in gelatin hydrogels. J. Biomed. Mater. Res., Part A 104, 1387-1397 (2016).

29. Seo, B. B., Choi, H., Koh, J. T. & Song, S. C. Sustained BMP-2 delivery and injectable bone regeneration using thermosensitive polymeric nanoparticle hydrogel bearing dual interactions with BMP-2. J. Controlled Release 209, 67-76 (2015).

30. Ma, C., Chang, B., Jing, Y., Kim, H. & Liu, X. Bio-inspired micropatterned platforms recapitulate 3D physiological morphologies of bone and dentinal cells. Adv. Sci. (Weinh) 5, 1801037 (2018).

31. Zhu, L., Luo, D. & Liu, Y. Effect of the nano/microscale structure of biomaterial scaffolds on bone regeneration. Int. J. Oral Sci. 12, 6 (2020).

32. Yoon, S. Chang, J., Kwon, N., Moon, S., Park, Y., Han, K. H., Lim, B. & Lee, J. H. Multifunctional nanomaterial-alginate drug delivery and imaging system for cancer therapy. Biochip J. 13, 236-242 (2019).

33. Ramon-Azcon, J., Ahadian, S., Obregon, R., Camci-Unal, G., Ostrovidov, S., Hosseini, V., Kaji, H., Ino, K., Shiku, H., Khademhosseini, A. & Matsue, T. Gelatin methacrylate as a promising hydrogel for 3D microscale organization and proliferation of dielectrophoretically patterned cells. Lab Chip 12, 2959-2969 (2012).

34. Kim, J. M., Kim, W. J., Kim, M. Y., Kim, K. P., Sim, S. J. & Kim, S. K. Development of hydrogel microparticle based RT-qPCR for advanced detection of BCR-ABL1 transcripts. Biochip J. 13, 182-190 (2019).

35. Sung, H., Ferlay, J., Siegel, R. L., Laversanne, M., Soerjomataram, I., Jemal, A. & Bray, F. Global Cancer Statistics 2020: GLOBOCAN Estimates of Incidence and Mortality Worldwide for 36 Cancers in 185 Countries. CA Cancer J Clin 71, 209-249, (2021)

36. Park, J. W., Kang, S. B., Hao, J., Lim, S. B., Choi, H. S., Kim, D. W., Chang, H. J., Kim, D. Y., Jung, K. H., Kim, T. Y., Kang, G. H., Chie, E. K., Kim, S. Y., Sohn, D. K., Kim, J. S., Lee, H. S., Kim, J. H., Jeong, S. Y. & Oh, J. H. Open versus laparoscopic surgery for mid or low rectal cancer after neoadjuvant chemoradiotherapy (COREAN trial): 10-year follow-up of an open-label, noninferiority, randomized controlled trial. Lancet Gastroenterol Hepatol 6, 569-577, (2021)

37. Romesser, P. B., Sherman, E. J., Whiting, K., Ho, M. L., Shaha, A. R., Sabra, M. M., Riaz, N., Waldenberg, T. E., Sabol, C. R., Ganly, I., McBride, S. M., Fagin, J. A., Zhang, Z., Tuttle, R. M., Wong, R. J. & Lee, N. Y. Intensity-modulated radiation therapy and doxorubicin in thyroid cancer: A prospective phase 2 trial. Cancer 127, 4161-4170, (2021)

38. Bae, J., Han, S. & Park, S. Recent advances in 3D bioprinted tumor microenvironment. BioChip Journal 14, 137-147, (2020)

5. Bayat Mokhtari, R., Homayouni, T. S., Baluch, N., Morgatskaya, E., Kumar, S., Das, B. & Yeger, H. Combination therapy in combating cancer. Oncotarget 8, 38022-38043, (2017)

39. Kumar, L., Harish, P., Malik, P. S. & Khurana, S. Chemotherapy and targeted therapy in the management of cervical cancer. Curr Probl Cancer 42, 120-128, (2018)

40. Kashkooli, F. M., Soltani, M. & Souri, M. Controlled anti-cancer drug release through advanced nano-drug delivery systems: Static and dynamic targeting strategies. J Control Release 327, 316-349, (2020)

41. Troendle, E. P., Khan, A., Searson, P. C. & Ulmschneider, M. B. Predicting drug delivery efficiency into tumor tissues through molecular simulation of transport in complex vascular networks. J Control Release 292, 221-234, (2018)

42. Jaragh-Alhadad, L., Behbehani, H. & Karnik, S. Cancer targeted drug delivery using active low-density lipoprotein nanoparticles encapsulated pyrimidines heterocyclic anticancer agents as microtubule inhibitors. Drug Delivery 29, 2759-2772, (2022)

43. Abdulridha, M. K., Al-Marzoqi, A. H., Al-Awsi, G. R. L., Mubarak, S. M. H., Heidarifard, M. & Ghasemian, A. Anticancer Effects of Herbal Medicine Compounds and Novel Formulations: a Literature Review. J Gastrointest Cancer 51, 765-773, (2020)

44. Andleeb, A., Andleeb, A., Asghar, S., Zaman, G., Tariq, M., Mehmood, A., Nadeem, M., Hano, C., Lorenzo, J. M. & Abbasi, B. H. A Systematic Review of Biosynthesized Metallic Nanoparticles as a Promising Anti-Cancer-Strategy. Cancers (Basel) 13, (2021)

45. Tay, K. C., Tan, L. T., Chan, C. K., Hong, S. L., Chan, K. G., Yap, W. H., Pusparajah, P., Lee, L. H. & Goh, B. H. Formononetin: A Review of Its Anticancer Potentials and Mechanisms. Front Pharmacol 10, 820, (2019)

46. Morelli, M. B., Bongiovanni, C., Da Pra, S., Miano, C., Sacchi, F., Lauriola, M. & D'Uva, G. Cardiotoxicity of Anticancer Drugs: Molecular Mechanisms and Strategies for Cardioprotection. Front Cardiovasc Med 9, 847012, (2022)

47. Chade, A. R. & Bidwell, G. L., 3rd. Novel Drug Delivery Technologies and Targets for Renal Disease. Hypertension 79, 1937-1948, (2022)

48. Qamar, Z., Qizilbash, F. F., Iqubal, M. K., Ali, A., Narang, J. K., Ali, J. & Baboota, S. Nano-Based Drug Delivery System: Recent Strategies for the Treatment of Ocular Disease and Future Perspective. Recent Pat Drug Deliv Formul 13, 246-254, (2019)

49. Qiu, X., Cao, K., Lin, T., Chen, W., Yuan, A., Wu, J., Hu, Y. & Guo, H. Drug delivery system based on dendritic nanoparticles for enhancement of intravesical instillation. Int J Nanomedicine 12, 7365-7374, (2017)

50. Rudsari, H. K., Veletic, M., Bergsland, J. & Balasingham, I. Targeted Drug Delivery for Cardiovascular Disease: Modeling of Modulated Extracellular Vesicle Release Rates. IEEE Trans Nanobioscience 20, 444-454, (2021)

51. Tang, H., Xiang, D., Wang, F., Mao, J., Tan, X. & Wang, Y. 5-ASA-loaded SiO2 nanoparticles—a novel drug delivery system targeting therapy on ulcerative colitis in mice. Mol Med Rep 15, 1117-1122, (2017)

52. Zhang, L., Shi, D., Shi, C., Kaneko, T. & Chen, M. Supramolecular micellar drug delivery system based on multi-arm block copolymer for highly effective encapsulation and sustained-release chemotherapy. J Mater Chem B 7, 5677-5687, (2019)

53. Ashique, S., Sandhu, N. K., Chawla, V. & Chawla, P. A. Targeted Drug Delivery: Trends and Perspectives. Curr Drug Deliv 18, 1435-1455, (2021)

54. Baveloni, F. G., Riccio, B. V. F., Di Filippo, L. D., Fernandes, M. A., Meneguin, A. B. & Chorilli, M. Nanotechnology-based Drug Delivery Systems as Potential for Skin Application: A Review. Curr Med Chem 28, 3216-3248, (2021)

55. Ford Versypt, A. N., Pack, D. W. & Braatz, R. D. Mathematical modeling of drug delivery from autocatalytically degradable PLGA microspheres—a review. J Control Release 165, 29-37, (2013)

56. Mansor, N. I., Nordin, N., Mohamed, F., Ling, K. H., Rosli, R. & Hassan, Z. Crossing the Blood-Brain Barrier: A Review on Drug Delivery Strategies for Treatment of the Central Nervous System Diseases. Curr Drug Deliv 16, 698-711, (2019)

57. Mohammadipour, F., Kiani, A. & Amin, A. The High Potency of Polymeric Nanoparticles in the Drug Delivery System for Hypertension Treatment: A Systematic Review. Curr Hypertens Rev 18, 54-63, (2022)

58. Puccetti, M., Pariano, M., Renga, G., Santarelli, I., D'Onofrio, F., Bellet, M. M., Stincardini, C., Bartoli, A., Costantini, C., Romani, L., Ricci, M. & Giovagnoli, S. Targeted Drug Delivery Technologies Potentiate the Overall Therapeutic Efficacy of an Indole Derivative in a Mouse Cystic Fibrosis Setting. Cells 10, (2021)

59. Salari, N., Faraji, F., Torghabeh, F. M., Faraji, F., Mansouri, K., Abam, F., Shohaimi, S., Akbari, H. & Mohammadi, M. Polymer-based drug delivery systems for anticancer drugs: A systematic review. Cancer Treat Res Commun 32, 100605, (2022)

60. Aberoumandi, S. M., Mohammadhosseini, M., Abasi, E., Saghati, S., Nikzamir, N., Akbarzadeh, A., Panahi, Y. & Davaran, S. An update on applications of nanostructured drug delivery systems in cancer therapy: a review. Artif Cells Nanomed Biotechnol 45, 1-11, (2017)

61. Daniyal, M., Liu, B. & Wang, W. Comprehensive Review on Graphene Oxide for Use in Drug Delivery System. Curr Med Chem 27, 3665-3685, (2020)

62. Dong, P., Rakesh, K. P., Manukumar, H. M., Mohammed, Y. H. E., Karthik, C. S., Sumathi, S., Mallu, P. & Qin, H. L. Innovative nano-carriers in anticancer drug delivery—a comprehensive review. Bioorg Chem 85, 325-336, (2019)

63. Kakkar, V., Verma, M. K., Saini, K. & Kaur, I. P. Nano Drug Delivery in Treatment of Oral Cancer, A Review of the Literature. Curr Drug Targets 20, 1008-1017, (2019)

64. Li, Z., Tan, S., Li, S., Shen, Q. & Wang, K. Cancer drug delivery in the nano era: An overview and perspectives (Review). Oncol Rep 38, 611-624, (2017)

65. Liu, B., Yang, W., Che, C., Liu, J., Si, M., Gong, Z., Gao, R. & Yang, G. A Targeted Nano Drug Delivery System of AS1411 Functionalized Graphene Oxide Based Composites. ChemistryOpen 10, 408-413, (2021)

66. Meschi, S. S., Farghadan, A. & Arzani, A. Flow topology and targeted drug delivery in cardiovascular disease. J Biomech 119, 110307, (2021)

67. Pinelli, F., Ortola, O. F., Makvandi, P., Perale, G. & Rossi, F. In vivo drug delivery applications of nanogels: a review. Nanomedicine (Lond) 15, 2707-2727, (2020)

68. Satapathy, S. & Patro, C. S. Solid Lipid Nanoparticles for Efficient Oral Delivery of Tyrosine Kinase Inhibitors: A Nano Targeted Cancer Drug Delivery. Adv Pharm Bull 12, 298-308, (2022)

69. Soica, C., Trandafirescu, C., Danciu, C., Muntean, D., Dehelean, C. & Simu, G. New improved drug delivery technologies for pentacyclic triterpenes: a review. Protein Pept Lett 21, 1137-1145, (2014)

70. Arauna, D., Vijayakumar, S. & Duran-Lara, E. Latest Advances in Hydrogel-Based Drug Delivery Systems for Optimization of Metabolic Syndrome Treatment. Curr Med Chem 28, 6274-6286, (2021)

71. Chatterjee, S. & Hui, P. C. Review of Applications and Future Prospects of Stimuli Responsive Hydrogel Based on Thermo-Responsive Biopolymers in Drug Delivery Systems. Polymers (Basel) 13, (2021)

72. Hani, U., Osmani, R. A., Bhosale, R. R., Shivakumar, H. G. & Kulkarni, P. K. Current Perspectives on Novel Drug Delivery Systems and Approaches for Management of Cervical Cancer: A Comprehensive Review. Curr Drug Targets 17, 337-352, (2016)

73. How, K. N., Yap, W. H., Lim, C. L. H., Goh, B. H. & Lai, Z. W. Hyaluronic Acid Mediated Drug Delivery System Targeting for Inflammatory Skin Diseases: A Mini Review. Front Pharmacol 11, 1105, (2020)

74. Hsu, X. L., Wu, L. C., Hsieh, J. Y. & Huang, Y. Y. Nanoparticle-Hydrogel Composite Drug Delivery System for Potential Ocular Applications. Polymers (Basel) 13, (2021)

75. Sonker, M., Bajpai, S., Khan, M. A., Yu, X., Tiwary, S. K. & Shreyash, N. Review of Recent Advances and Their Improvement in the Effectiveness of Hydrogel-Based Targeted Drug Delivery: A Hope for Treating Cancer. ACS Appl Bio Mater 4, 8080-8109, (2021)

76. Villalba-Rodriguez, A. M., Parra-Saldivar, R., Ahmed, I., Karthik, K., Malik, Y. S., Dhama, K. & Iqbal, H. M. N. Bio-inspired Biomaterials and their Drug Delivery Perspectives-A Review. Curr Drug Metab 18, 893-904, (2017)

77. Wani, S. U. D., Gautam, S. P., Qadrie, Z. L. & Gangadharappa, H. V. Silk fibroin as a natural polymeric based bio-material for tissue engineering and drug delivery systems A review. Int J Biol Macromol 163, 2145-2161, (2020)

78. Abbasalizadeh, F., Alizadeh, E., Bagher Fazljou, S. M., Torbati, M. & Akbarzadeh, A. Anticancer Effect of Alginate-chitosan Hydrogel Loaded with Curcumin and Chrysin on Lung and Breast Cancer Cell Lines. Curr Drug Deliv 19, 600-613, (2022)

79. David, L., Dulong, V., Le Cerf, D., Cazin, L., Lamacz, M. & Vannier, J. P. Hyaluronan hydrogel: an appropriate three-dimensional model for evaluation of anticancer drug sensitivity. Acta Biomater 4, 256-263, (2008)

80. Rezk, A. I., Obiweluozor, F. O., Choukrani, G., Park, C. H. & Kim, C. S. Drug release and kinetic models of anticancer drug (BTZ) from a pH-responsive alginate polydopamine hydrogel: Towards cancer chemotherapy. Int J Biol Macromol 141, 388-400, (2019)

81. Wang, Q., Zhang, H., Xu, H., Zhao, Y., Li, Z., Li, J., Wang, H., Zhuge, D., Guo, X., Xu, H., Jones, S., Li, X., Jia, X. & Xiao, J. Novel multi-drug delivery hydrogel using scar-homing liposomes improves spinal cord injury repair. Theranostics 8, 4429-4446, (2018)

Technical Problem

According to many clinical researches, it is known that a bone morphogenetic protein is directly helpful for regeneration of damaged bone tissue and formation of bone and anticancer drugs effectively kill a cancer. Many studies have been actively made to develop a delivery system for the bone morphogenetic protein or the anticancer drugs.

Meanwhile, in the related art, a method of delivering the bone morphogenetic protein or anticancer drug have performed by using a form of a hydrogel, a microsphere, a nanoparticle, a fiber, and the like configured with a material such as a metal, a ceramic, a polymer, and a composite. In addition, these materials are intended to be dissolved in a desired site. However, there is a problem called a side effect, and there is a limit in the quantitative, localized delivery of the bone morphogenetic protein or anticancer drug.

Solution to Problem

In order to solve the above-described problems, the present invention is to provide a method of controlling local release of target compounds containing a bone morphogenetic protein or anticancer drug by patterning a hydrogel onto an electrospun nanoporous membrane. Preferably, the method includes steps of: (S1) preparing a micromold with a plurality of concave grooves; (S2) pouring a hydrogel solution comprising the target compounds into the micromold; (S3) filling the plurality of concave grooves on the micromold with the hydrogel solution; (S4) covering an electrospun nanoporous membrane on the micromold filled with the hydrogel solution; (S5) patterning a hemispherical hydrogel onto the electrospun nanoporous membrane by crosslinking the hydrogel onto the electrospun nanoporous membrane; and (S6) detaching the micromold from the hemispherical hydrogel patterned electrospun nanoporous membrane wherein the hemispherical hydrogel is at a concentration selected from the group consisting of 2.5% (w/v), 5% (w/v), 10% (w/v) and 15% (w/v), and wherein the hemispherical hydrogel is configured to control release of the target compounds based on the hydrogel concentration.

In addition, the hydrogel contains target compound and at least one of gelatin methacryloyl (gel-MA), hyaluronic acid, Na-alginate and hyaluronic acid methacrylate (HAMA).

In addition, the target compounds are at a concentration selected from 1-2000 ng/mL.

In addition, the electrospun nanoporous membrane is manufactured by an electrospinning process using dissolving polyurethane and Pluronic® F-127 (Poloxamer 407) to a concentration of 10% (w/v) and 10% (w/v) of solvent.

In addition, the electrospun nanoporous membrane has the surface wettability as the contact angle 82.89±1.3°.

In addition, the cross-linking is executed by exposing UV light (wavelength 360 nm, intensity 10,000 $mW/cm^2$) and hydrophilic functional groups selected from the group consisting of —OH, —COOH, and —NH) of the hydrogel and the electrospun nanoporous membrane control the hemispherical hydrogel array onto the electrospun nanoporous membrane.

In order to solve the above-described problems, the present invention is to provide a method of controlling local release of target compounds containing a bone morphogenetic protein or anticancer drug by patterning a hydrogel onto an electrospun amphipathic nanoporous membrane.

Preferably, the method includes steps of: (S1) preparing a micromold with a plurality of concave grooves; (S2) pouring a hydrogel solution comprising the target compounds into the micromold; (S3) filling the plurality of concave grooves on the micromold with the hydrogel solution; (S4) covering a hydrophilic layer of electrospun amphipathic nanoporous membrane on the micromold filled with the hydrogel solution; (S5) patterning a hemispherical hydrogel onto the electrospun amphipathic nanoporous membrane by crosslinking the hydrogel onto the electrospun amphipathic nanoporous membrane; and (S6) detaching the micromold from the hemispherical hydrogel patterned electrospun amphipathic nanoporous membrane wherein the hemispherical hydrogel is at a concentration selected from the group consisting of 2.5% (w/v), 5% (w/v), 10% (w/v) and 15% (w/v), and wherein the hemispherical hydrogel is configured to control release of the target compounds based on the hydrogel concentration.

In addition, the hydrogel contains target compound and at least one of gelatin methacryloyl (gel-MA), hyaluronic acid, Na-alginate and hyaluronic acid methacrylate (HAMA).

In addition, the target compounds are at a concentration selected from 1~ 2000 ng/ml.

In addition, the electrospun amphipathic nanoporous membrane is comprising of hydrophobic layer and hydrophilic layer.

Preferably, the hydrophobic layer is manufactured by electrospinning process using dissolving polyurethane to a concentration of 10% (w/v) solvent.

Preferably, the hydrophilic layer is manufactured by an electrospinning process on the hydrophobic layer using dissolving polyurethane and Pluronic® F-127 (Poloxamer 407) to a concentration of 10% (w/v) and 10% (w/v) of solvent.

In addition, the hydrophilic layer has the surface wettability as the contact angle 82.89±1.3°.

In addition, the cross-linking is executed by exposing UV light (wavelength 360 nm, intensity 10,000 $mW/cm^2$) and hydrophilic functional groups selected from the group consisting of —OH, —COOH, and —NH) of the hydrogel and the hydrophilic layer of electrospun amphipathic nanoporous membrane control the hemispherical hydrogel array onto the electrospun amphipathic nanoporous membrane.

Advantageous Effects of Invention

According to the present invention, it is possible to control local release of a bone morphogenetic protein or anticancer by using a hemispherical hydrogel patterned electrospun nanoporous membrane which can serve as a carrier of the bone morphogenetic protein or the anticancer. The bone morphogenetic protein is essentially used in orthopedic and dental fields and the anticancer drug effectively kill a cancer. But the delivery method of the bone morphogenetic protein or the anticancer drug is not quantitative and causes a lot of side effects. However, in the present invention, a delivery method and process capable of performing local release quantitatively can be applied in the clinical field. In addition, it is also expected that the present invention can be used for a case where quantitative release of a drug inside and outside a human body is required.

DETAILED DESCRIPTION

Figure 1:
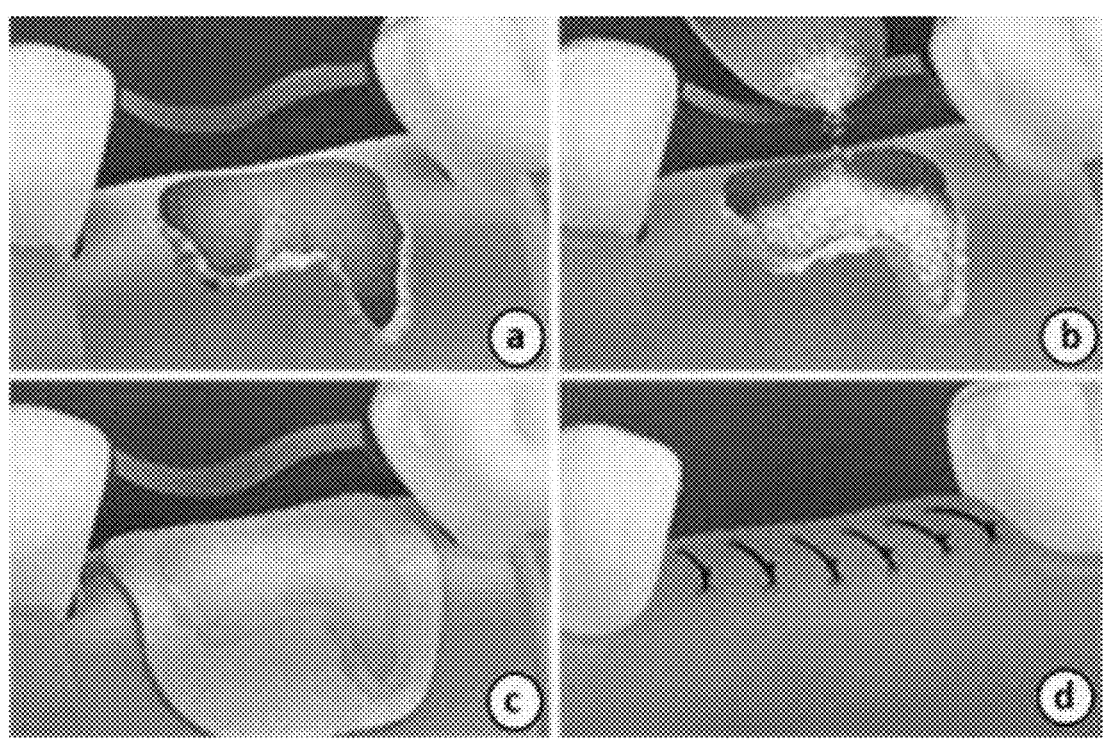
FIG. 1 is a diagram illustrating a commonly used restoration process and a nanoporous membrane for regeneration of bone.

Hereinafter, a preferred embodiment of the present invention will be described in detail with a manufacturing process.

It should be noted that the specific numerical values given as examples are only for explaining the technical idea of the present invention in more detail, and that the technical idea of the present invention is not limited thereto and that various modifications are possible.

In addition, in the specification of the present invention, the same components are denoted by the same reference numerals, and those components which are well known in the technical field and can be easily created by the ordinary skilled in the art will be omitted in detailed description.

The present invention provides a method of controlling local release of target compounds containing a bone morphogenetic protein or anticancer drug by patterning a hydrogel onto an electrospun nanoporous membrane.

Preferably, the method includes steps of: (S1) preparing a micromold with a plurality of concave grooves; (S2) pouring a hydrogel solution comprising the target compounds into the micromold; (S3) filling the plurality of concave grooves on the micromold with the hydrogel solution; (S4) covering an electrospun nanoporous membrane on the micromold filled with the hydrogel solution; (S5) patterning a hemispherical hydrogel onto the electrospun nanoporous membrane by crosslinking the hydrogel onto the electrospun nanoporous membrane; and (S6) detaching the micromold from the hemispherical hydrogel patterned electrospun nanoporous membrane wherein the hemispherical hydrogel is at a concentration selected from the group consisting of 2.5% (w/v), 5% (w/v), 10% (w/v) and 15% (w/v), and wherein the hemispherical hydrogel is configured to control release of the target compounds based on the hydrogel concentration.

More preferably, the hemispherical hydrogel is at a concentration 2.5% (w/v) and the hemispherical hydrogel is configured to control release of the target compounds based on the hydrogel concentration.

In addition, the hydrogel contains target compound and at least one of gelatin methacryloyl (gel-MA), hyaluronic acid, Na-alginate and hyaluronic acid methacrylate (HAMA). Preferably, the hydrogel contains target compound and at least one of gelatin methacryloyl (gel-MA) and hyaluronic acid methacrylate (HAMA). More preferably, the hydrogel contains target compound and gelatin methacryloyl (gel-MA).

In addition, the target compounds are at a concentration selected from 1-2000 ng/ml. Preferably, the target compounds are at a concentration selected from 500-2000 ng/ml. More preferably, the target compounds are at a concentration selected from 1000-2000 ng/mL. More preferably, the target compounds are at a concentration 2000 ng/mL.

In addition, the electrospun nanoporous membrane is manufactured by an electrospinning process using dissolving polyurethane and Pluronic® F-127 (Poloxamer 407) to a concentration of 10% (w/v) and 10% (w/v) of solvent.

In addition, the electrospun nanoporous membrane has the surface wettability as the contact angle 82.89±1.3°.

In addition, the cross-linking is executed by exposing UV light (wavelength 360 nm, intensity 10,000 mW/cm$^2$) and hydrophilic functional groups selected from the group consisting of —OH, —COOH, and —NH) of the hydrogel and the electrospun nanoporous membrane control the hemispherical hydrogel array onto the electrospun nanoporous membrane.

The present invention provides a method of controlling local release of target compounds containing a bone morphogenetic protein or anticancer drug by patterning a hydrogel onto an electrospun amphipathic nanoporous membrane.

Preferably, the method includes steps of: (S1) preparing a micromold with a plurality of concave grooves; (S2) pouring a hydrogel solution comprising the target compounds into the micromold; (S3) filling the plurality of concave grooves on the micromold with the hydrogel solution; (S4) covering a hydrophilic layer of electrospun amphipathic nanoporous membrane on the micromold filled with the hydrogel solution; (S5) patterning a hemispherical hydrogel onto the electrospun amphipathic nanoporous membrane by cross-linking the hydrogel onto the electrospun amphipathic nanoporous membrane; and (S6) detaching the micromold from the hemispherical hydrogel patterned electrospun amphipathic nanoporous membrane wherein the hemispherical hydrogel is at a concentration selected from the group consisting of 2.5% (w/v), 5% (w/v), 10% (w/v) and 15% (w/v), and wherein the hemispherical hydrogel is configured to control release of the target compounds based on the hydrogel concentration.

In addition, the hydrogel contains target compound and at least one of gelatin methacryloyl (gel-MA), hyaluronic acid, Na-alginate and hyaluronic acid methacrylate (HAMA). Preferably, the hydrogel contains target compound and at least one of gelatin methacryloyl (gel-MA) and hyaluronic acid methacrylate (HAMA). More preferably, the hydrogel contains target compound and hyaluronic acid methacrylate (HAMA).

In addition, the target compounds are at a concentration selected from 1-2000 ng/ml. Preferably, the target compounds are at a concentration selected from 500-2000 ng/ml. More preferably, the target compounds are at a concentration selected from 1000-2000 ng/mL. More preferably, the target compounds are at a concentration 2000 ng/mL.

In addition, the electrospun amphipathic nanoporous membrane comprises a hydrophobic layer and hydrophilic layer. Preferably, the hydrophobic layer is manufactured by an electrospinning process using dissolving polyurethane to a concentration of 10% (w/v) solvent. More preferably, the hydrophilic layer is manufactured by an electrospinning process on the hydrophobic layer using dissolving polyurethane and Pluronic® F-127 (Poloxamer 407) to a concentration of 10% (w/v) and 10% (w/v) of solvent.

In addition, the hydrophilic layer has the surface wettability as the contact angle 82.89±1.3°.

In addition, the cross-linking is executed by exposing UV light (wavelength 360 nm, intensity 10,000 mW/cm2) and hydrophilic functional groups selected from the group consisting of —OH, —COOH, and —NH) of the hydrogel and the hydrophilic layer of electrospun amphipathic nanoporous membrane control the hemispherical hydrogel array onto the electrospun amphipathic nanoporous membrane.
Local Release of Bone Morphogenetic proteins Using Patterning Hydrogel to Nanoporous Membrane
Materials and Methods
PDMS Concave Micromold for Micropatterning A polymeric concave micromold was used to facilitate BMP-2 immobilization into the gelatin methacrylate (GelMA) hydrogel.

For fabricating a PDMS (Dow Corning, MI, USA)-based concave micromold using a replication process, a well-defined photo-lithography method was used with the photosensitive epoxy resin (SU-8, Micro Chem, MA, USA). A hemispheric SU-8 polymeric convex master mold, which commonly uses an epoxy-based negative photoresist according to a published protocol, was used.

Briefly, to make a master mold, a perforated SU-8 shadow mask layer with arrayed holes (diameter: 250 μm) was designed. The perforated SU-8 shadow layer was exposed to UV light for SU-8 polymerization with the designed photo mask film. Following curing and development of the SU-8 photoresist, the Kapton film and SU-8 were separated from a Si-wafer, and the Kapton film was carefully removed from the SU-8 photoresist layer, which was used as a shadow mask. The radius of each pattern was 250 μm, and they appeared at intervals of 250 μm.

Finally, to replicate the concave micromold, the PDMS solution was mixed at a 10 (base): 1.2 (curing agent) weight ratio. The mixed solution was stirred for 10 min with a stirring stick and vacuumed to eliminate residual bubbles. The PDMS solution was poured into the prepared SU-8 master mold, and heated to 80° C. for 30 min. Then, after annealing to the hotplate, the replicated PDMS concave micromold was separated from the SU-8 master mold.
Hydrogel Micropatterns on Nanoporous Membrane Localized GelMA hydrogel patterning was performed via in situ photo-polymerization using prepared the PDMS concave micromold and electrospun nanoporous membrane (semi-permeable membrane, SNM).

Figure 2:
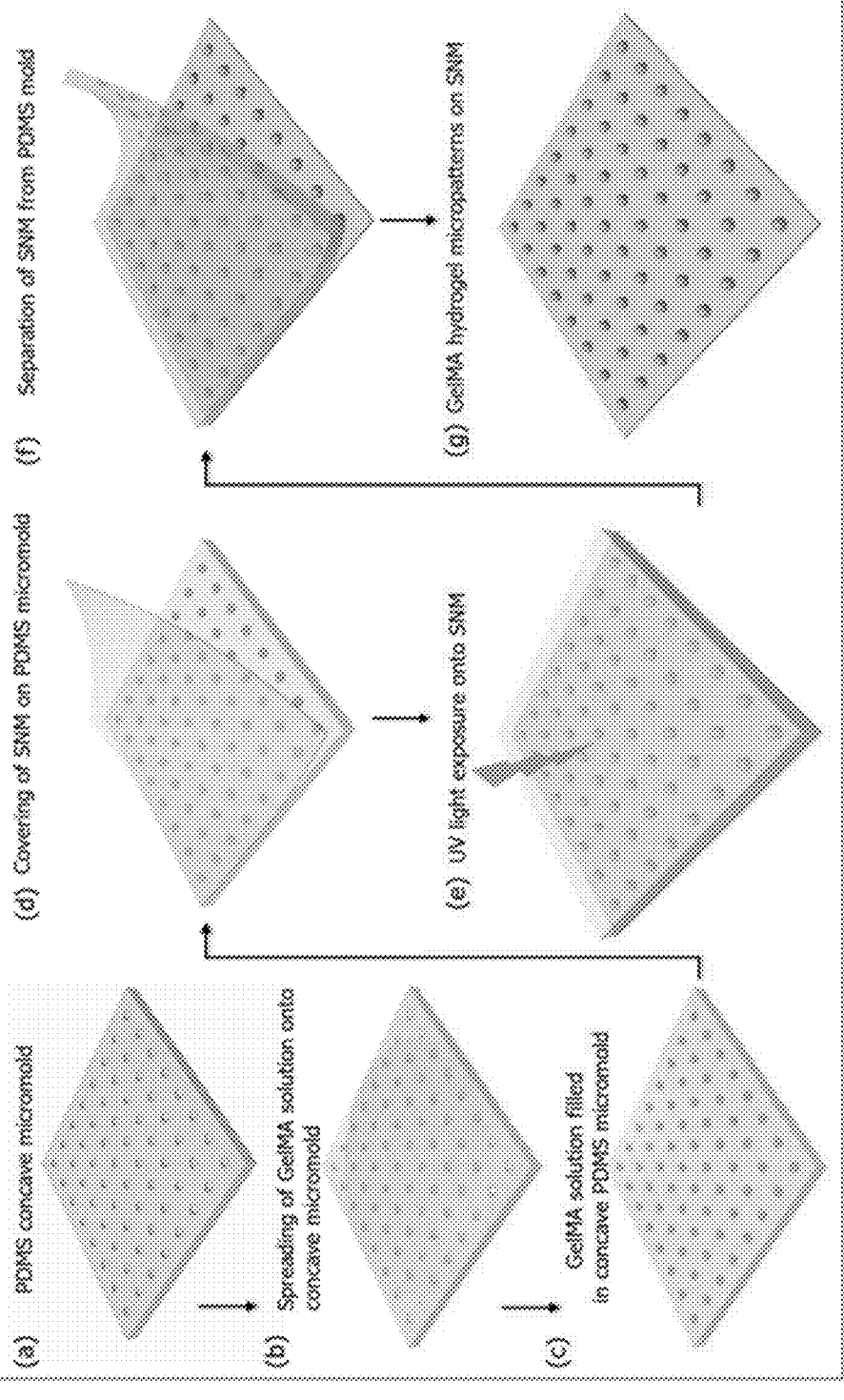
FIG. 2 illustrates formation of hydrogel micropatterns on the nanoporous membrane.
Figure 4:
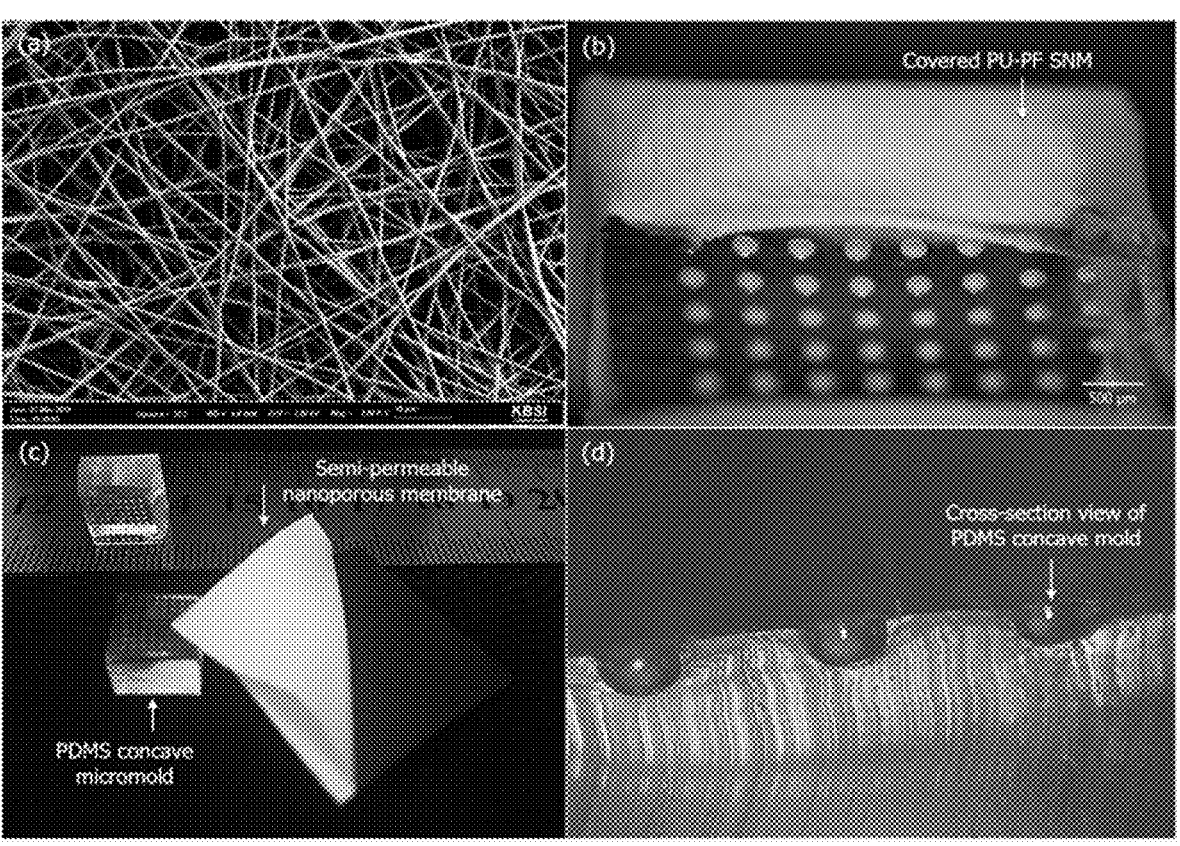
FIG. 4 illustrates image of electrospun PU-PF SNM.

After autoclaving (for sterilization), the surfaces of the PDMS concave micromold and SNM were treated with 60 W oxygen plasma (Cute, Femto-Science, Inc.) for easy filling and adsorption of GelMA solution (FIG. 2 (b), (c)). Then, 1 mL of 2.5% (w/v), 5% (w/v), and 10% (w/v) GelMA solution was filled onto the PDMS mold and the excess solution was removed using a rubber scraper. Next, SNM (15×15 mm) was used to cover the PDMS concave micromold. For photo-crosslinking the SNM, the covered SNM surface was exposed to UV light (Omnicure S2000, Maritimes, Canada) (wavelength: 360 nm, intensity: 10,000 mW/cm²) at distance of 8 cm for 30 s. The photo-crosslinked GelMA hydrogel micropatterns were obtained by peeling the SNM from the PDMS mold as shown in FIG. 4 (b), (c).

Figure 5:
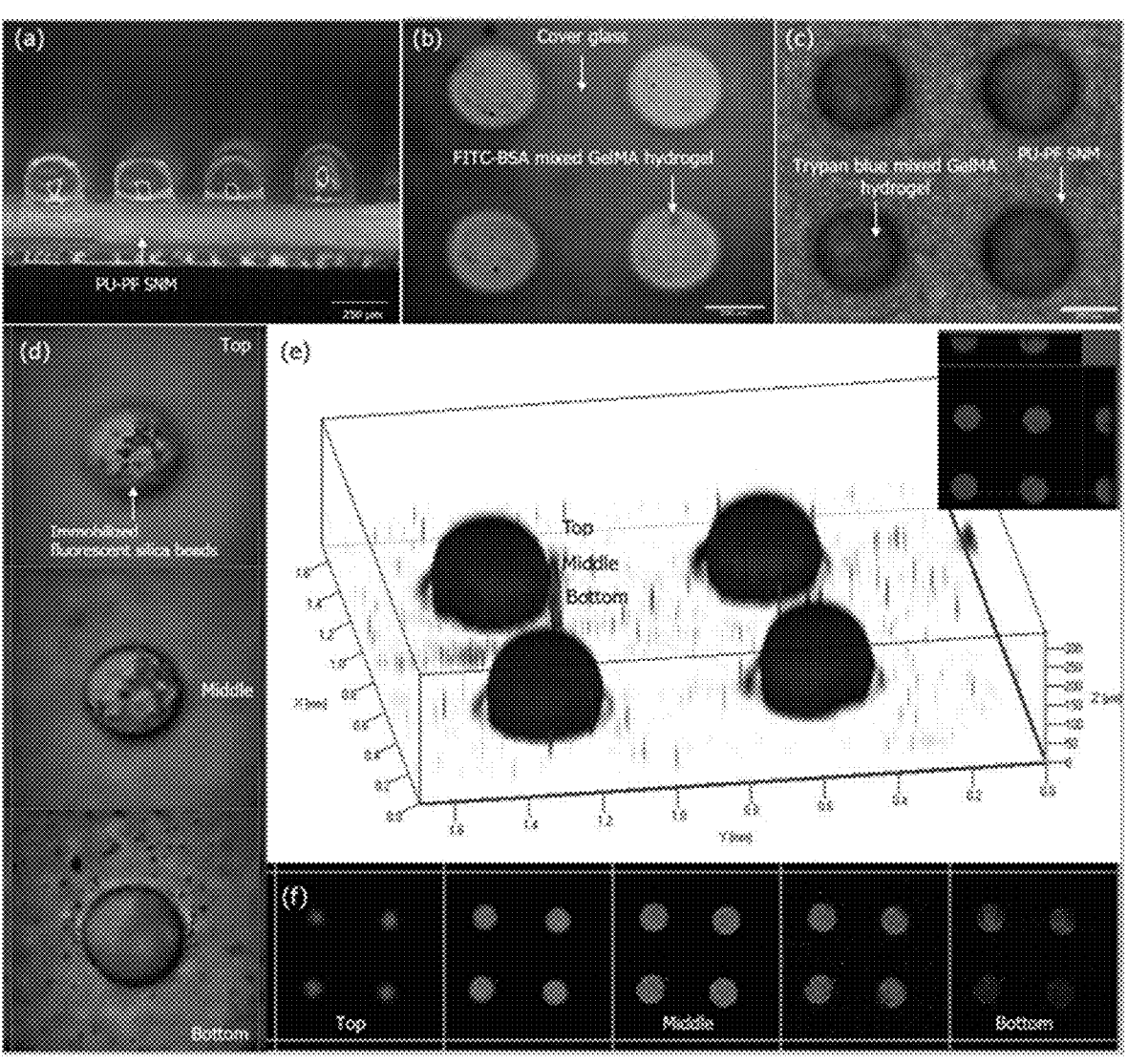
FIG. 5 illustrates Micropatterned hydrogel onto nanoporous membrane.

As shown in FIG. 5 (b), (c), to observe and visualize the photo-cross-linked GelMA hydrogel micropatterns on SNM, 2.5% (w/v) GelMA solution was mixed with trypan blue (Sigma-Aldrich, St, Louis, MO, USA) and FITC-BSA (70 kDa) (Sigma-Aldrich) solution. In addition, to determine the BMP-2 immobilization ability of various materials, 5 μm fluorescent silica beads were mixed and cross-linked with the GelMA hydrogel and scanned using confocal microscopy. The images were analyzed to determine whether the beads were homogeneously dispersed in the hemispherical micropatterned GelMA hydrogel (FIG. 5 (d), (e), (f)).

To produce the electrospun semi-permeable membrane (SNM), the solution was obtained by dissolving polyurethane (PU) and Pluronic® F-127 (Poloxamer 407) (Sigma-Aldrich)] to a concentration of 10% (w/v) and 10% (w/v) of solvent. The mixture was stirred at 65° C. for 24 h until all the solutes were dissolved. For electrospinning, 10 ml of the PU-PF solution was prepared in a 10 ml syringe with the use of a metal spinneret needle of 23 G; this aliquot was then electrospun at a flow rate of 0.4 ml/h at an applied voltage set at 13.5 kV The metal-based collector was located 40 cm away from the spinneret needle and was rotated at 10 revolutions per minute for 60 h. The SNM was dried in an oven at 60° C. for 4 h, and was exposed to UV light for 10 h to sterilize it.

Mechanical Properties and Adhesion Stability

A digital force gauge meter (FGV-50XY, Shimpo Co. Japan) was used for the measurement of the compressive strength of the micropatterned GelMA hydrogel on the SNM. Deformation was observed by pressing the micropatterned GelMA hydrogel with the tip of an ink pen. Simultaneously, for evaluating the adhesion between the GelMA hydrogel micropatterns and the SNM surface, the GelMA hydrogel micropatterned SNM was stretched several times in the horizontal, vertical, and diagonal directions and the separation of the GelMA micropattern from the SNM was. In addition, the tensile strength was examined using a micro-universal testing machine (UTM) (LR10K-plus, Lloyd Instruments Ltd., UK) under a crosshead speed of 50 mm/min at room temperature. The specimens were prepared as rectangles (10×50 mm) containing GelMA hydrogel micropatterns. During the testing, a moisturizing mist was intermittently sprayed onto the specimens to prevent dehydration of the GelMA hydrogel.

Estimation of the Release Profile of BMP-2 from the Micropatterned GelMA Hydrogel To assess the fundamental release profile determining the concentration of the GelMA hydrogel, the Millington and Quirk model for drug transport was theoretically studied using a computational porous material with effective transport properties. The surroundings were modeled in the shape of a rectangle of 500 µm width and 1000 µm height, while the actual depth of the culture medium in the experiments was several orders of magnitude higher than the height of the surroundings of the simulation. Therefore, the top boundary condition of the surroundings was defined to be of the external convection type of flux with a mass transfer coefficient. The boundary condition of both sides was set to no flux of drugs through the boundary via diffusion from the neighboring surroundings. The bottom surface of the surrounding was also under no flux condition. The half-circular boundary of the surroundings adjacent to the GelMA top surface was assumed to have the same concentration as that of the surface. A simple 2D model analyzed using the COMSOL® Multiphysics software, a commercial finite element method (FEM)-based simulation tool (version 5.4, module Chemical Species Transport and Transport of Diluted Species in Porous Media, COMSOL Inc., Burlington, MA, USA), was used for numerical analysis to emulate the diffusive transfer of BMP-2 in GelMA hydrogel under three different concentrations. As the actual size of the pores in hydrogel materials is typically several orders of magnitude smaller than the model domain to be analyzed and is difficult to be described in detail, a simple 2D porous model with effective porosity was defined using the simulation. The equation for the time-dependent model is based on the Millington and Quirk diffusivity model as follows:

$$\frac{\partial c}{\partial t} + \nabla \cdot [-(D_D + D_e)]\nabla c = 0$$

$$D_e = \frac{\epsilon_p}{\tau_F} D_F$$

where c denotes the concentration (% w/v), $D_D$ the dispersion coefficient (m²/s), $D_e$ the diffusion coefficient (m²/s), $\epsilon_p$ the porosity, $T_F$ the effective diffusivity which is equal to $\epsilon^{-1/3}$, and DF the fluid diffusion coefficient (m²/s). This computational simulation solves only diffusion and dispersion problem by mass transfer in porous media due to concentration gradient, and no forced convection mechanism was considered in the GelMA hydrogel domain. The initial condition of drug concentration was set to $c_{sur}$ ($t_0$)=0.

Figure 6:
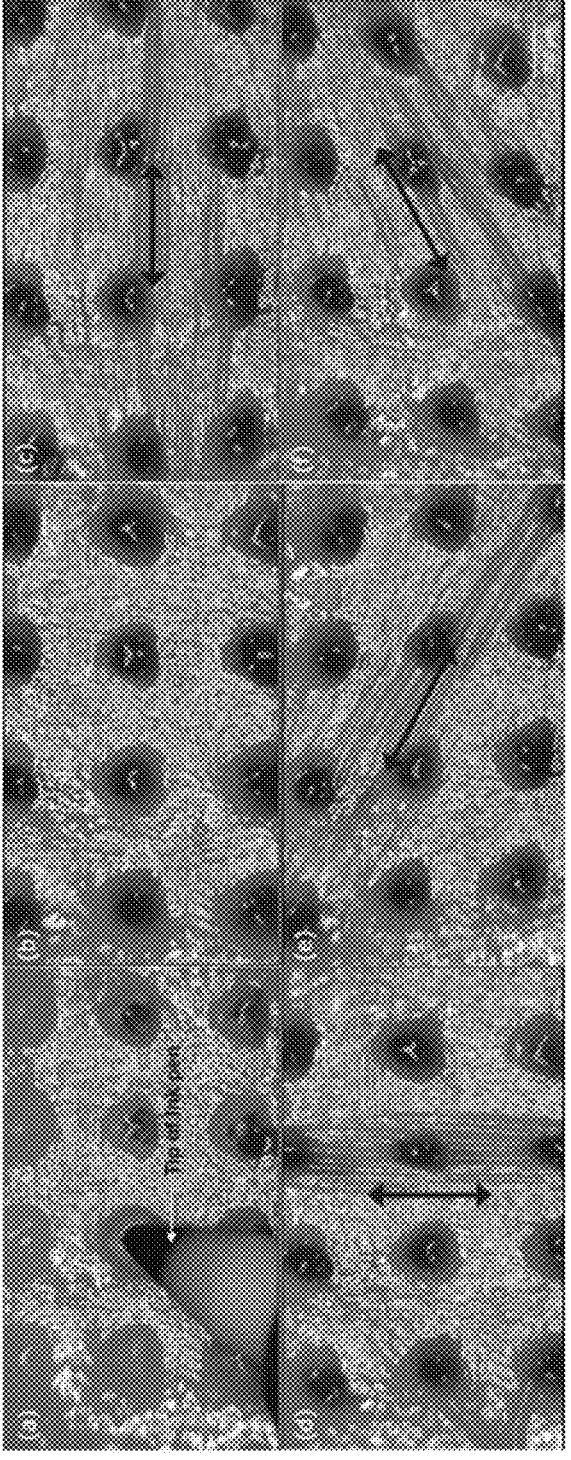
FIG. 6 illustrates compressive strength and adhesion tests.

As shown in FIG. 6 (a)-(c), both GelMA and the surroundings were discretized in 2D-triangular meshes using predefined extra fine element size with maximum diameter of 20 µm. For high accuracy and rapid convergence of the results, the half-circular boundary between patterned GelMA hydrogel and the surroundings were also discretized using the boundary layer properties, with 8 layers for both sides and boundary layer stretching factor of 1.2. The maximum element size was 5 µm. The structure of GelMA hydrogel micropattern model for the simulation is assumed to be a half circle with a radius of 125 µm, and the space between the neighboring structures is 250 µm, which is based on the actual patterned GelMA hydrogel dimensions.

Instead of simulating the full-scale actual micropattern (8 by 8), only one structure and the surroundings in the vicinity were analyzed. The initial condition of drug concentration in the GelMA hydrogel domain is defined as a constant, c(t0)=c0. The boundary condition at the bottom surface of the GelMA hydrogel was set to no flux of drug through the boundary, while the external convection flux was considered the boundary condition at the top surface, which was not due to forced convective flux, but due to diffusion arising from the concentration differences between the micropattern and the surroundings as described in the following equation.

$$-(D_D+D_e)\nabla_C \cdot \vec{n} = k_m(c-c_{sur})$$

Where $\vec{n}$ denotes the normal vector, $k_m$ is the mass transfer coefficient (m/s) in GelMA, and $c_{sur}$ denotes the concentration [% (m/v)] in the surrounding domain. In addition, to predict the release profile of BMP-2 (30 kDa) (which will be immobilized later), the release profile of FITC-BSA (70 kDa) from the micropatterned GelMA hydrogel was assessed using an inverted fluorescence microscope (Axiovert 200M, Carl Zeiss, Darmstadt, Germany).

Figure 7:
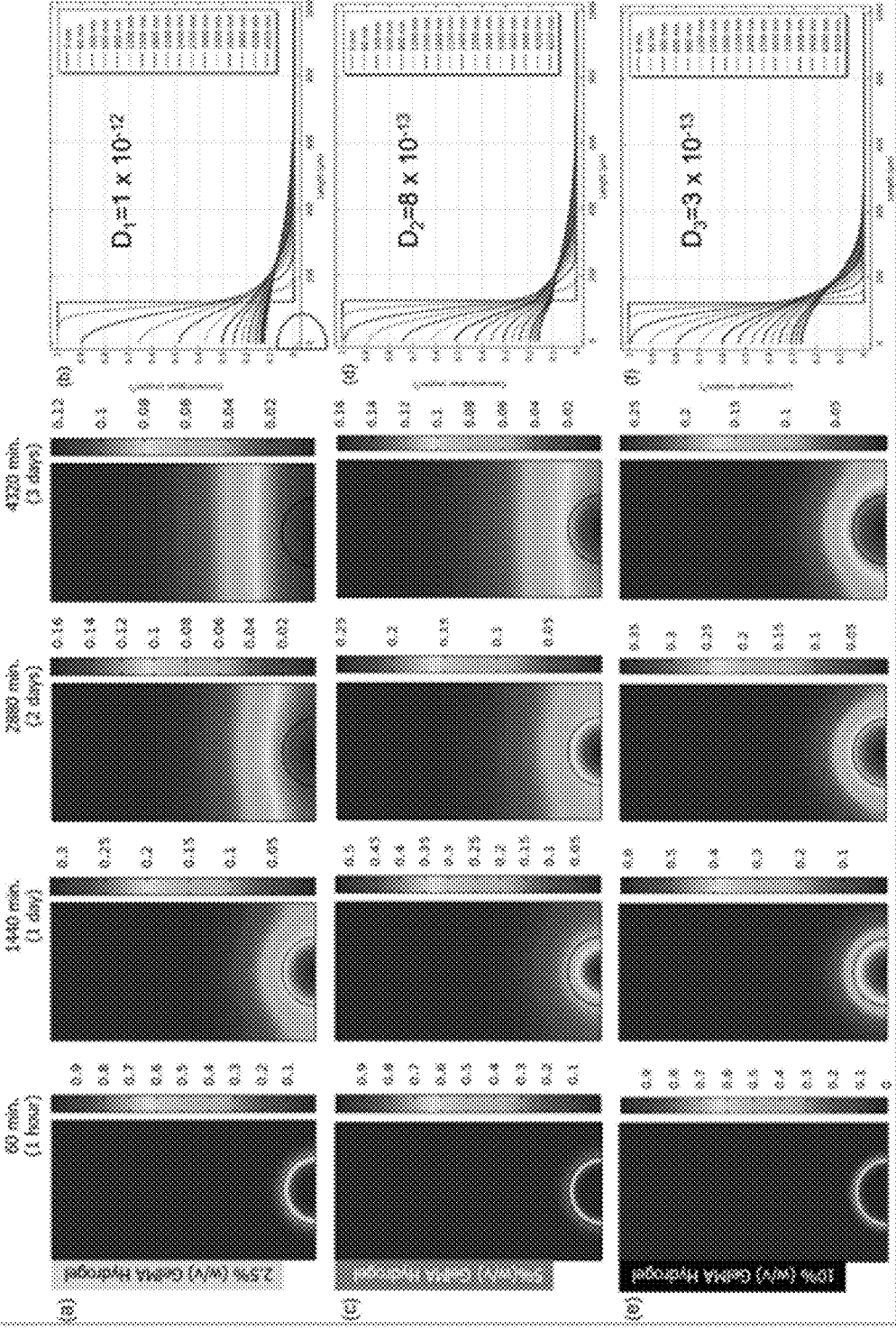
FIG. 7 illustrates computational simulation model based on the Millington and Quirk diffusivity model.

The samples were prepared with the lowest, middle, and highest concentrations of GelMA solution (2.5, 5, and 10% w/v) (FIG. 7). To emulate the in vivo condition, 3 mL PBS solution was changed each time after sampling over 6 days. The same spot of each sample was monitored daily to observe the changes in the fluorescence intensity of FITC-BSA measured over time.

Evaluation of Osteogenic Differentiation and Morphology

To evaluate the effect of osteogenic differentiation, including morphology, on the localized and controlled release of BMP-2, human osteoblast-like MG-63 cells (American Type Culture Collection, Rockville, MD, USA) were cultured onto the GelMA hydrogel micropatterned SNM for 6 days.

In particular, before the pattering process, the SNM was fixed onto the bottom of the cell culture dish using half-cured PDMS solution and dried for preventing the floating of SNM in the culture media. The cell density was 1×10⁶ cells/mL, and 100 µL cells were seeded onto the BMP-2 (2000 ng/ml)-immobilized GelMA hydrogel micropatterned SNM. In addition, MG-63 cells were simultaneously cultured on SNM without BMP-2 as the control group. The cells were cultured in cell media [10% (w/w) Dulbecco's modified Eagle's medium (DMEM)] (Gibco, CA, USA) supplemented with 1% (w/w) fetal bovine serum (FBS) (Gibco) and 1% (w/w) penicillin/streptomycin (Gibco) in a humidified atmosphere containing 5% $CO_2$ at 37° C.

After 6 days, the actin filaments were stained with Alexa Fluor 568 phalloidin fluorescent dye (Invitrogen, Eugene, OR, USA) to determine the cytoskeletal organization in MG-63 cells. Image-iT™ FX signal enhancer was used to enhance the signal-to-noise ratio of fluorescently labeled cells, and fluorescent images were acquired and processed using an Axiovert 200 inverted microscope.

Osteogenic differentiation was evaluated by staining the calcium deposits using the ARS staining kit (pH 4.1-4.3; Sigma-Aldrich). First, the culture medium was removed, and the cells were gently washed thrice with PBS. Next, the cells were fixed with 4% (w/v) formaldehyde for 15 min at room temperature. Then, the cells were washed with distilled water, followed by the addition of 2% (w/v) solution of 60 mM ARS, the pH to 4.1-4.3 of which was adjusted using $NH_4OH$ and HCl solutions. After filtering the ARS solution with a 0.2 μm filter, 1 mL of the ARS solution was dropped onto the SNMs and incubated for 1 h at 4° C. Then, the stained cells were photographed to analyze the calcium deposits induced by released BMP-2.

Result

Hydrophilic PU-PF SNM

FIG. 2 illustrates a formation of GelMA hydrogel micropatterns on the semi-permeable nanoporous membrane; (a)-(c) filling of GelMA solution into the PDMS concave micromold, (d)-(e) UV light exposure of the GelMA solution for crosslinking with the mold through the covered membrane, and (f)-(g) GelMA hydrogel micropatterns on the membrane after separation of the mold.

The present invention provides a method of controlling local release of target compounds containing a bone morphogenetic protein or anticancer drug by patterning a hydrogel onto an electrospun nanoporous membrane, wherein the patterning of the hydrogel onto the electrospun nanoporous membrane includes; (S1) preparing a micromold with a plurality of concave grooves; (S2) pouring a hydrogel solution comprising the target compounds into the micromold; (S3) filling the plurality of concave grooves on the micromold with the hydrogel solution; (S4) covering an electrospun nanoporous membrane on the micromold filled with the hydrogel solution; (S5) patterning a hemispherical hydrogel onto the electrospun nanoporous membrane by crosslinking the hydrogel onto the electrospun nanoporous membrane; and (S6) detaching the micromold from the hemispherical hydrogel patterned electrospun nanoporous membrane wherein the hemispherical hydrogel is at a concentration selected from the group consisting of 2.5% (w/v), 5% (w/v), 10% (w/v) and 15% (w/v), and wherein the hemispherical hydrogel is configured to control release of the target compounds based on the hydrogel concentration.

The cross-linking in the step (S5) is performed by any one of a photo cross-linking method using light or an ion cross-linking method using ion exchange. Preferably, The cross-linking in the step (S5) is performed by a photo cross-linking method using UV light (wavelength 360 nm, intensity 10,000 mW/cm²). Based on cross-linking, hydrophilic functional groups selected from the group consisting of —OH, —COOH, and —NH) of the hydrogel and the electrospun nanoporous membrane control the hemispherical hydrogel array onto the electrospun nanoporous membrane.

Preferably, the present invention provides a method of controlling local release by patterning a hydrogel on a electrospun nanoporous membrane, wherein the micromold of step (S1) is made of any one of polydimethylsiloxane (PDMS), Teflon, and polymethylmethacrylate (PMMA).

In the preliminary test with hydrophobic polyurethane (PU)-based SNM as the substrate, the GelMA solution was partially cross-linked and did not attach onto the SNM. This indicated that for the GelMA hydrogel to cross-link and adhere onto the SNM, the GelMA solution has to be sufficiently absorbed between the SNM prior to crosslinking. However, the GelMA solution did not completely penetrate the interstitial space of the SNM because of its strong hydrophobicity in pure PU SNM. Hence, we attempted to improve the wettability of pure PU SNM using polyethylene oxide (PEO)-based Pluronic® F-127 (Poloxamer 407) blending. The novel hydrophilic PU-PF SNM with a uniform nanofiber diameter was successfully produced without droplets, as observed using scanning electron microscopy (FIG. 4 (*a*)). The diameter of the randomly oriented average nanofiber ranged from 200 nm to 500 nm, and inter-fiber pores were uniformly generated throughout the PU-PF SNM. In terms of altered surface wettability, the contact angle recorded on the PU SNM surface was 82.89±1.3°; however, in PU-PF SNM, the liquid droplets spread completely on the surface, corresponding to a contact angle of 0° due to extension of PEO chains, as reported previously.

The attenuated total reflection Fourier-transform infrared (ATR-FTIR) spectroscopy analysis revealed quantitative information regarding the blended PF. A C—O bond appeared at 1103 cm$^{-1}$ in the hydrophilic PU-PF SNM, which increased due to the presence of PF. These results show that semipermeable physical properties with high porosity are sufficient for transmitting ultra-violet (UV) for crosslinking of GelMA hydrogels.

The hydrogel contains target compound and at least one of gelatin methacryloyl (gel-MA), hyaluronic acid, Na-alginate and hyaluronic acid methacrylate (HAMA). Preferably, The hydrogel contains target compound and gelatin methacryloyl (Gel-MA).

The synthesized GelMA hydrogel was confirmed using an ATR-FTIR spectra. The identified methacrylation spectra of gelatin were similar to that reported previously, except for a broad peak for the hydroxyl group at 3,500 cm$^{-1}$ and subdued peaks at 1,000~1,700 cm$^{-1}$ for the GelMA hydrogel, which can be attributed to the —OH group, indicating that both peaks originated from the C=C bonds.

Micropatterning for GelMA Hydrogel

Figure 3:
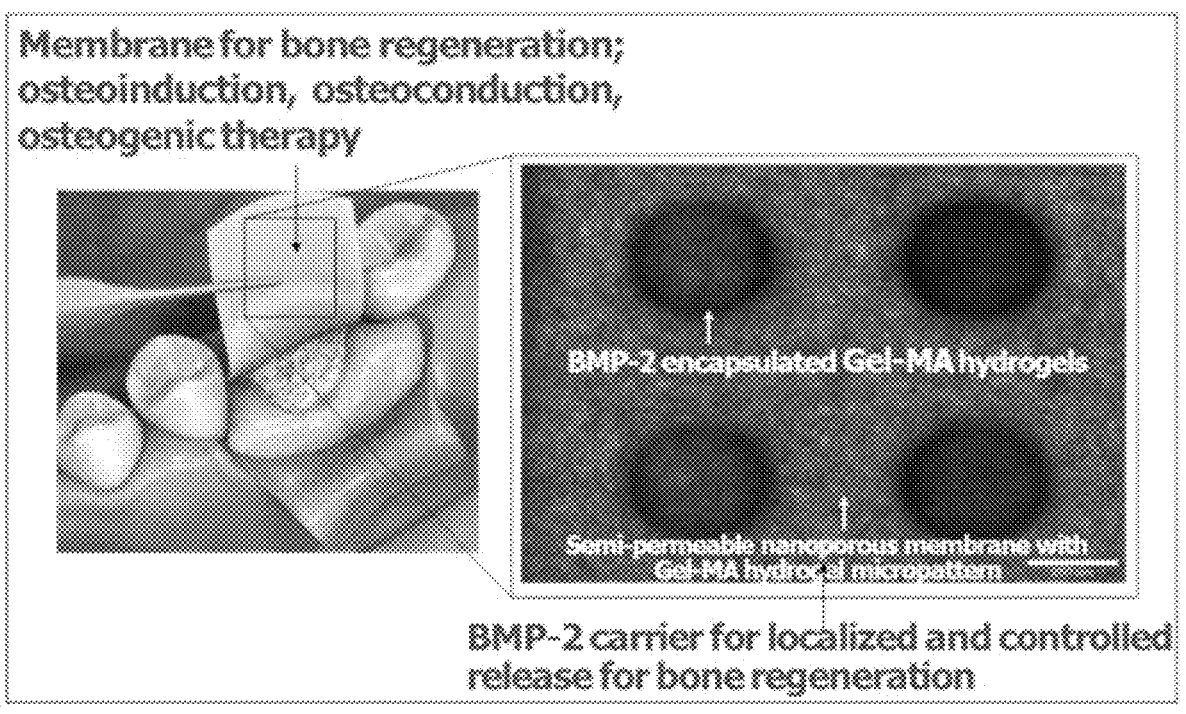
FIG. 3 illustrates a carrier of a bone morphogenetic protein in hydrogel and a pattern on a nanoporous membrane according to the present invention.

FIG. 3 illustrates the carrier of the bone morphogenetic protein in hydrogel and the pattern on the nanoporous membrane according to the present invention.

The present invention provides a method of controlling local release of target compounds containing a bone morphogenetic protein or anticancer drug by patterning a hydrogel onto an electrospun nanoporous membrane, wherein the patterning of the hydrogel onto the electrospun nanoporous membrane includes; (S1) preparing a micromold with a plurality of concave grooves; (S2) pouring a hydrogel solution comprising the target compounds into the micromold; (S3) filling the plurality of concave grooves on the micromold with the hydrogel solution; (S4) covering an electrospun nanoporous membrane on the micromold filled with the hydrogel solution; (S5) patterning a hemispherical hydrogel onto the electrospun nanoporous membrane by crosslinking the hydrogel onto the electrospun nanoporous membrane; and (S6) detaching the micromold from the hemispherical hydrogel patterned electrospun nanoporous membrane wherein the hemispherical hydrogel is at a concentration selected from the group consisting of 2.5% (w/v), 5% (w/v), 10% (w/v) and 15% (w/v), and wherein the hemispherical hydrogel is configured to control release of the target compounds based on the hydrogel concentration.

The micromold may be made of polydimethylsiloxane (PDMS), Teflon, or polymethylmethacrylate (PMMA). Preferably, the micromold may be made of polydimethylsiloxane (PDMS)

The SNM are manufactured according to biodegradable and non-biodegradable methods by using biopolymers of polyurethane and polylactide-co-glycolide (PLGA), which have been approved by the US Food and Drug Administration, for in vivo transplantation. The SNM is manufactured by an electrospinning process.

In addition, for local release of the bone morphogenetic protein or anticancer drug, patterning by using cross-linking of hydrogel with excellent biocompatibility is used. In the present invention, a cross-linking method, there are used a photo cross-linking method using UV light. The material used was hydrogel patterned with gelatin methacryloyl (gel-MA), hyaluronic acid, and Na-alginate. Preferably, The material used was hydrogel patterned with gelatin methacryloyl (gel-MA). The hydrogel patterning is performed by using the bone morphogenetic protein or anticancer drug contained in the hydrogel in accordance with each condition.

In addition, for the patterning, a master mold for supporting hydrogel is required. On the other hand, various master molds are manufactured through a soft-lithography process and a 3D printing process. From the manufactured master mold (intaglio), a replica mold (embossing) is manufactured by using a photomicrograph (PDMS) with excellent biocompatibility and excellent optical transparency. The above-mentioned hydrogel is inserted into the replica mold formed as an embossing mold. A SNM manufactured by electrospinning is covered with the mold. The hydrogel is formed by UV light transmission and thus, various patterns containing the bone morphogenetic protein or anticancer drug is manufactured.

This can be confirmed in FIG. 4 illustrating a photograph (b) of an intaglio PDMS mold replicated with PDMS and an intaglio PDMS mold covered with a SNM and a photograph (d) of a cross section of the intaglio PDMS mold.

The concentration of the target compound used can be selected widely depending on the shape, size, and type of the pattern.

In addition, with respect to the membrane, the release rate of the carried target compound can be also controlled by using a biodegradable membrane and a non-biodegradable membrane.

FIG. 5 illustrates micropatterned GelMA hydrogel. (a) Optical image of SNM, (b) FITC-BSA mixed fluorescence image on cover-glass, (c) Trypan-blue mixed GelMA micropattern on SNM, (d) fluorescent micro-particles immobilized on GelMA micropattern on cover-glass, (e) confocal microscopy Z-stack of rhodamine B mixed micropatterned GelMA hydrogel, and (f) image of gallery view of rhodamine B mixed micropatterned GelMA hydrogel on cover-glass.

Based on the polydimethylsiloxane (PDMS) concave mold, the single pattern size of the GelMA hydrogel was 250 µm, although the actual average size was approximately 270 µm on the image due to the swelling of the GelMA hydrogel. As shown in FIG. 5a, the GelMA hydrogel showed successfully hemispheric cross-linking on flat smooth cover glass surface, as well as on porous mesh-like PU-PF SNM. In FIG. 5 (b), (c), the addition of fluorescent labeled FITC-BSA and trypan blue confirmed that the micropatterns were clearly formed only in the targeted region, indicating that crosslinking and patterning were possible even if suitable materials were added to the GelMA hydrogel. FIG. 5 (d), (e)

shows the Z stack image observed using a confocal laser microscope. When the fixed micro-beads were monitored while moving along the Z-axis, we observed that the fluorescent beads were evenly dispersed in the pattern. These results involve that even if BMP-2 is immobilized and patterned in the GelMA hydrogel, it can be immobilized stably and homogeneously therein. The GelMA hydrogel was intact even after pressing it with the tip of an ink pen (FIG. 6). FIG. 6 illustrates the compressive strength and adhesion tests: (a-b) Compressed GelMA hydrogel micropatterns on SNM, (c-d) horizontal and vertical stretching test, and (e-f) diagonally stretched SNM containing GelMA hydrogel micropatterns. The compressive strength was determined from both the crosslinking density of the GelMA hydrogel and the adhesion between the GelMA hydrogel and SNM. The compressive strengths were 1.064 MPa at the lowest concentration (2.5% w/v), 4.556 MPa at the middle concentration (5% w/v), and 6.504 MPa at the highest concentration (10% w/v). If the compressive strength is weak, the surrounding environment and hydrostatic pressure may crack the GelMA hydrogel pattern. On the contrary, if the strength is too high, the slow release of BMP-2 can be suppressed due to the high density of GelMA; however, the value measured in this experiment has been analyzed previously and found to be suitable for controlled BMP-2 release without affecting the GelMA pattern as a viscoelastic material. Even when the same specimen was pulled horizontally lengthwise and diagonally, the patterned GelMA hydrogel remained reliably attached and did not separate from the SNM. These results showed that GelMA hydrogels are strongly attached, cross-linked, and patterned on the surface of the three-dimensional network-based SNM using the novel method proposed in the study.

Cross-Linking for the BMP-2 Encapsulated GelMA Micropatterning on SNM

As predicted, the hemisphere radius tended to decrease with increase in the concentration of the GelMA hydrogel and BMP-2, and accurate patterning was formed as the hydrophilicity of SNM increased. Although the increase in UV irradiation intensity and exposure time was increased at high concentration of the GelMA hydrogel, the pattern completeness could not be improved significantly. When hydrophobic SNM was used, it remained in the PDMS mold without adhesion to SNM at all GelMA hydrogel concentrations. However, the adhesion pattern was partially observed in the hydrophilic SNM, although the concentration of the GelMA hydrogel was increased. To confirm the possibility of loading of BMP-2 in the GelMA hydrogel, fluorescent beads and FITC-BSA were used instead of BMP-2 (which is transparent and difficult to observe), and pattern formation was observed with increasing GelMA hydrogel concentration. At the lowest concentration, the FITC-BSA distribution was uniform throughout the pattern; however, at the highest concentration of the GelMA hydrogel, FITC-BSA was observed locally. GelMA patterning containing BMP-2 on the surface of SNM requires hydrophilic rather than hydrophobic SNM, and it helps to penetrate the GelMA hydrogel rapidly and easily between membrane interlayers due to high surface tension. In addition, SNM as a substrate must possess sufficient transmittance to allow UV light to cross the GelMA in the PDMS mold through the SNM. As summarized in Table 1, change in BMP-2 concentration affected the pattern completeness of the GelMA hydrogel.

TABLE 1

| | | Concentration of GelMA Hydrogel | | | |
|---|---|---|---|---|---|
| | | 2.5% (w/v) | 5% (w/v) | 10% (w/v) | |
| Concentration of BMP-2 | 2000 ng/mL | Partial adhesion | Partial adhesion | Partial adhesion | PU SNM |
| | | Best cross-linking | Good cross-linking | Poor cross-linking | |
| | | Perfect adhesion | Good adhesion | Partial adhesion | PU-PF SNM |
| | | Best cross-linking | Best cross-linking | Poor cross-linking | |
| | 5000 ng/mL | No adhesion | Partial adhesion | No adhesion | PU SNM |
| | | Partial cross-linking | Partial cross-linking | Good cross-linking | |
| | | Good adhesion | Partial adhesion | Partial adhesion | PU-PF SNM |
| | | Partial cross-linking | Good cross-linking | Good cross-linking | |
| | 10000 ng/mL | No adhesion | No adhesion | No adhesion | PU SNM |
| | | Partial cross-linking | Partial cross-linking | Partial cross-linking | |
| | | No adhesion | Partial adhesion | Partial adhesion | PU-PF SNM |
| | | Partial cross-linking | Partial cross-linking | Partial cross-linking | |

Thus, the lowest concentration (2.5% w/v) of the GelMA hydrogel was used as the optimal condition for the best micropattern with 2000 ng/ml BMP-2.

Analysis of Localized and Controlled Release

FIG. 7 shows the computationally simulated time dependent drug concentration distribution, which depended on the drug diffusion coefficients in the GelMA hydrogel models, for 3 days (i.e., 4,320 min). This simulation analyzes how the diffusion-driven release of BMP-2 might occur from the micropatterned GelMA hydrogel models of different concentrations. As expected, BMP-2 diffuses from the GelMA hydrogel into the surrounding, including the culture medium, over time, and concentration distribution is affected by the diffusion coefficients. We simulated three different diffusion coefficient models and investigated the spatiotemporal variations of BMP-2 for the entire domain, including the GelMA hydrogel structure and the surrounding after every 60 min. At 60 min, BMP-2 molecules diffused slightly through the interface between the GelMA hydrogel and the surrounding, although the diffusion rates for each case appeared to differ slightly. At 1,440 min (1 day), the highest density model retained more BMP-2 (approximately 0.6 mol/m³) at the center of the patterned GelMA hydrogel, whereas other lower density models retained approximately 0.5 mol/m³ and 0.3 mol/m³. In the surroundings in the vicinity of the GelMA hydrogel boundary, the spatial distribution of BMP-2 for the lowest density model (2.5% w/v) shown in FIG. 7 (a) was distinct from that in the other higher density models shown in FIG. 7 (c), (e). More BMP-2 diffuse to the region lacking BMP-2 in the low density model than in the other higher density models. Furthermore, owing to the possible diffusion effects from the neighboring GelMA hydrogel micropatterns on both sides, fluxes through either side boundary were not observed. The distribution showed a convex-roof shape due to an upward movement along the side boundary. At 2,880 min (2 days), the BMP-2 distribution appeared to be apparently flat in the surroundings near the GelMA hydrogel pattern for the lowest density model. The highest density model (10% w/v, shown in FIG. 7 (e)) still maintained a semicircular shape of BMP-2 distribution, as high density of GelMA reduces diffusion of BMP-2 out of the patterned GelMA hydrogel into the surroundings. The middle density model (5% w/v, FIG. 5 (c)) also showed a gradually flattening BMP-2 distribution in the surrounding. On day 1, the concentrations at the center of each model decreased to half of the initial value. At 4,320 min (3 days), the highest density model finally showed a convex-roof shaped BMP-2 distribution curve in the surrounding, whereas almost flat BMP-2 distribution in the surroundings was observed for the other lower density models; this configuration is expected to be retained with gradual changes in concentration, to the end of boundary of the analysis domain over time. Interestingly, the concentrations of the highest density model were almost 2-fold higher than those of the lowest density model for 1, 2, and 3 days. As the BMP-2 release from the GelMA modeled as a 2D semicircle, the concentration of the drug in the GelMA gradually decreased over time due to diffusion, and the decrease rates differed with the densities of the GelMA hydrogel. Eventually, the BMP-2 concentration in the GelMA hydrogel approached that of the surrounding from the initial value. FIG. 7 (b), (d), (f) shows the spatiotemporal variations of BMP-2 concentrations along a hypothetical cut line connecting the centers of both the patterned GelMA hydrogel and the top boundary of the surrounding, as indicated in FIG. 7 (a), (c), (e). The initial concentration distribution shows a vertical drop at 125 μm corresponding to the pattern radius, indicating that BMP-2 molecules were uniformly distributed over the patterned volume. The diffusion occurred gradually into the surrounding. In the early stages, the distribution showed a steep gradient near the interface in both domains. As time progressed, the molecules permeated the surrounding and the gradient changed gradually. As expected, the highest concentration model (10% w/v) showed the slowest gradient variation in concentration than the other lower density (2.5 and 5% w/v) models. In addition, at the last stage, the concentration at the center for the highest density model was the highest, indicating that the extent of BMP-2 retention in the GelMA hydrogel was the strongest.

To determine whether the GelMA hydrogel micropattern can improve the sustainability of the BMP-2 drug carrier and to predict the release profile of BMP-2 from the GelMA hydrogel, FITC-BSA, instead of BMP-2 (similar amounts), was loaded on the hydrogel.

Figure 8:
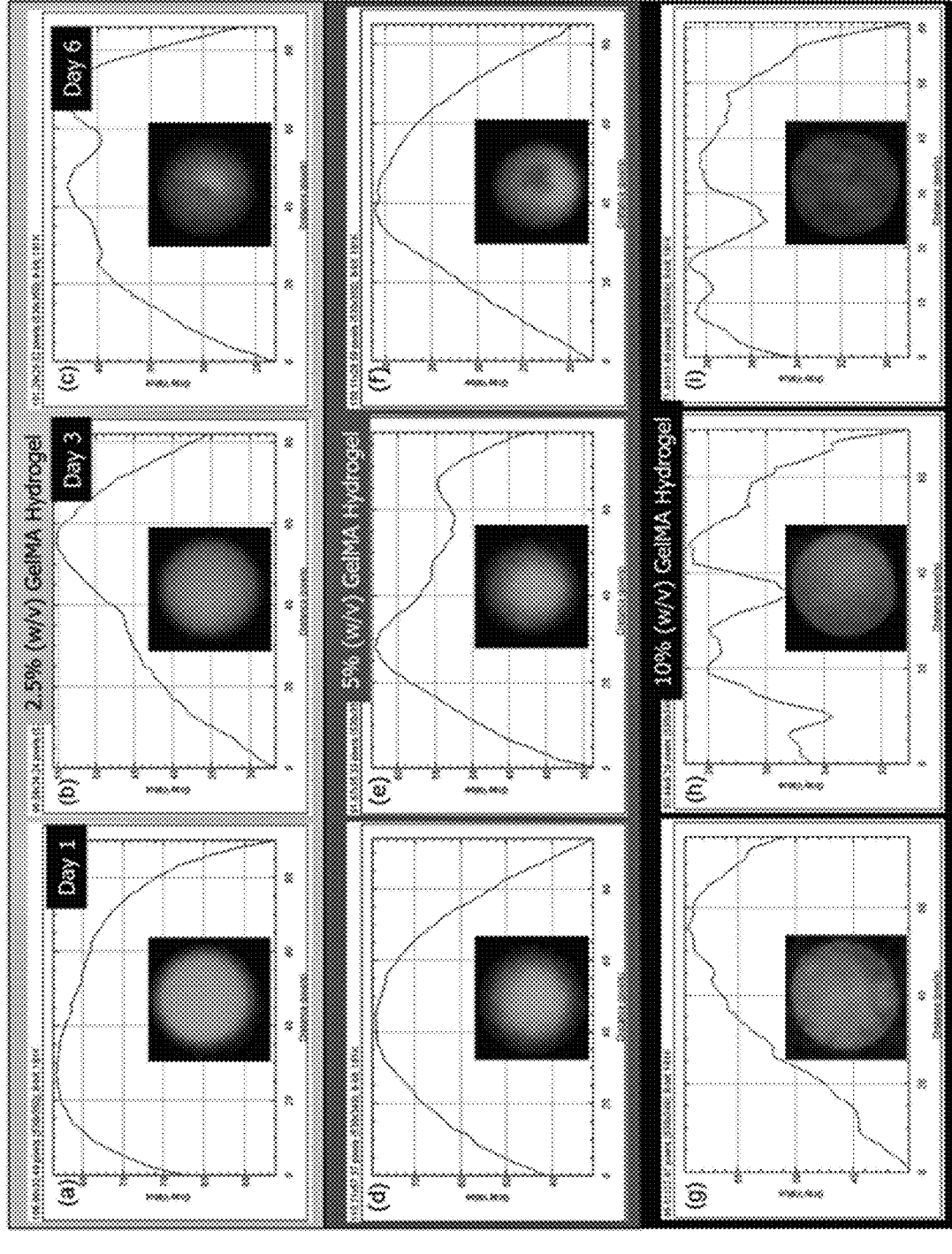
FIG. 8 illustrates charts obtained by tracking intensities of fluorescence for 6 days attenuated by release of a fluorescent material in hydrogel.

FIG. 8 illustrates charts obtained by tracking intensities of fluorescence for 6 days attenuated by release of a fluorescent material in hydrogel by using a fluorescent material in order to verify release control performance of a bone morphogenetic protein according to the present invention: (a-c) Lowest (2.5% w/v), (d-f) middle (5% w/v), (g-i) highest (10% w/v) concentration of GelMA hydrogel.

Using fluorescent microscopy, the amount of FITC-BSA (excitation: 485 nm/emission: 535 nm) released from the micropatterns to the outer phosphate buffered saline (PBS) due to difference in diffusion was measured over time and the emission amount was calculated for 6 days (FIG. 8).

Initially, each fixed FITC-BSA intensity was normalized to 100. As shown in FIGS. 8 (*a*), (*d*), and (*g*) on day 1, the low concentration case showed a rapid decrease of approximately 75% fluorescence intensity (25.1 a. u.) due to the convulsive diffusion at the initial stage, and kept the decreased intensity for 6 days (22.0 a. u. on day 3 and 21.7 a. u. on day 6). Even at the medium and high concentrations, the rapid decreases of about 65% (35.2 a. u.) and 52% (49.1 a. u.), respectively, were observed only on the first day. On the 3rd day, the reduction rates of only 4% (34.3 a. u.) and 6% (45.2 a. u.) were observed, comparable to the first day (FIGS. 8 (*b*), (*e*), and (*h*)), and only the smallest reduction rates of 5% (33.7 a. u.) and 7% (44.1 a. u.) were recorded on the last 6th day, respectively (FIGS. 8 (*c*), (*f*), and (*i*)). It has been known that when the hydrogel is cross-linked, the swelling of the hydrogel is maximized for 24 hours. As the concentration of the hydrogel decreases, the swelling degree increases and the density decreases, whereas the swelling degree decreases and the density increases when the concentration increases. Thus, the swelling of the GelMA hydrogel by cross-linking results in the volume changes of the patterns and redistribution of density within the patterns. Under the same diffusion condition, the diffusive transfer of FITC-BSA at the low concentration of GelMA is rapidly and easily made toward PBS solution. At the medium and high concentrations, the initial diffusion rates are shown to be lowered by about 10% and 23%, respectively, due to the relatively high density of the patterns. Although the experiments lasted for 6 days, the results were consistent with those of the typical and ideal drug release profiles, which shows burst release in low density carriers and sustained release in high density carriers.

Figure 9:
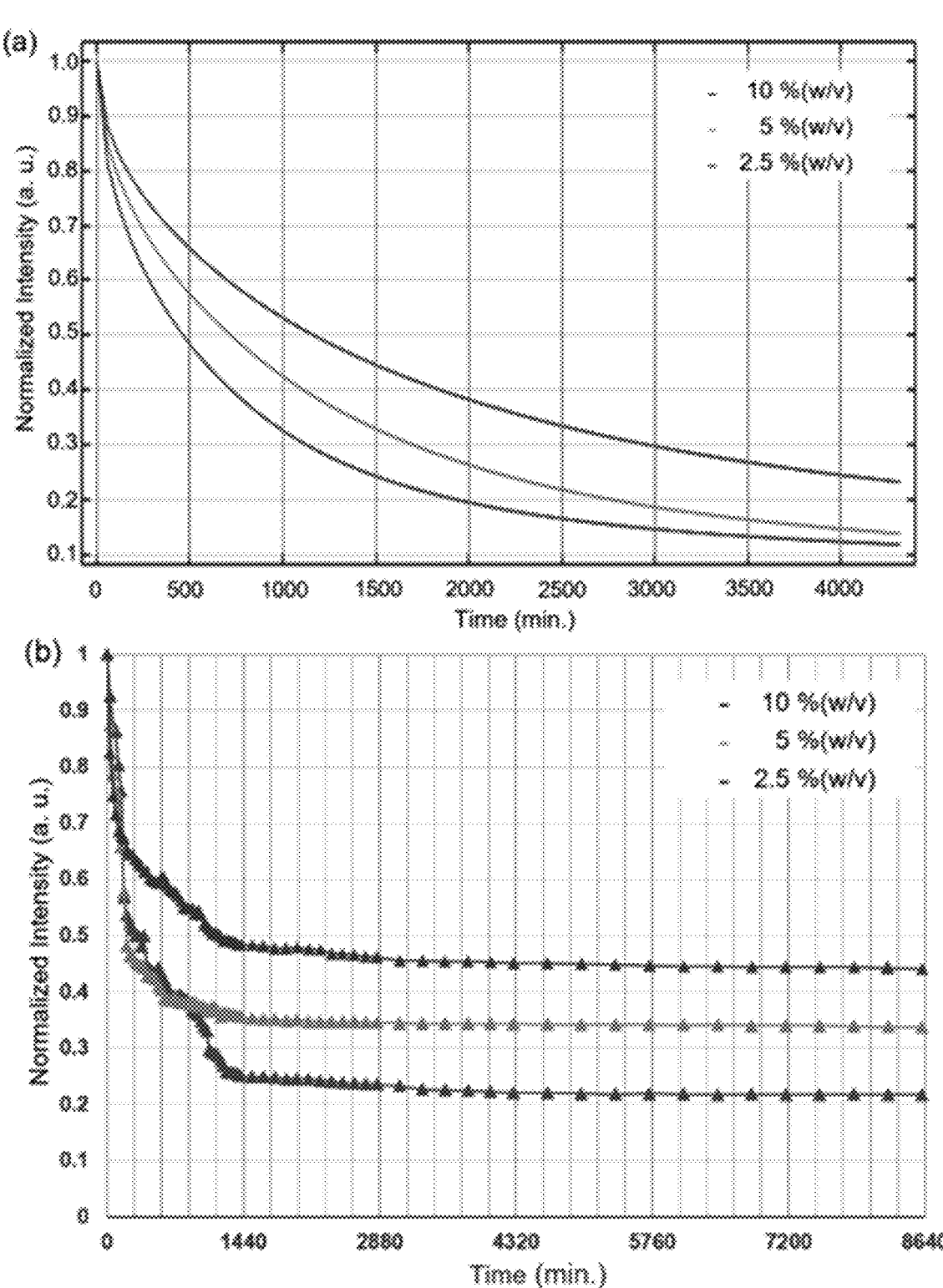
FIG. 9 illustrates release control values verified by using a bone morphogenetic protein and a hydrogel concentration.

FIG. 9 illustrates release control values verified by using a bone morphogenetic protein and a hydrogel concentration. In detail, it is expended that, the higher the concentration of the hydrogel, the lower the release rate of the drug, and the lower the concentration of the hydrogel, the higher the release rate of the drug. In addition, it is expected that the release rate depends on the concentration of the bone morphogenetic protein.

Osteogenic Differentiation of MG-63 Cells After BMP-2 Release

Figure 10:
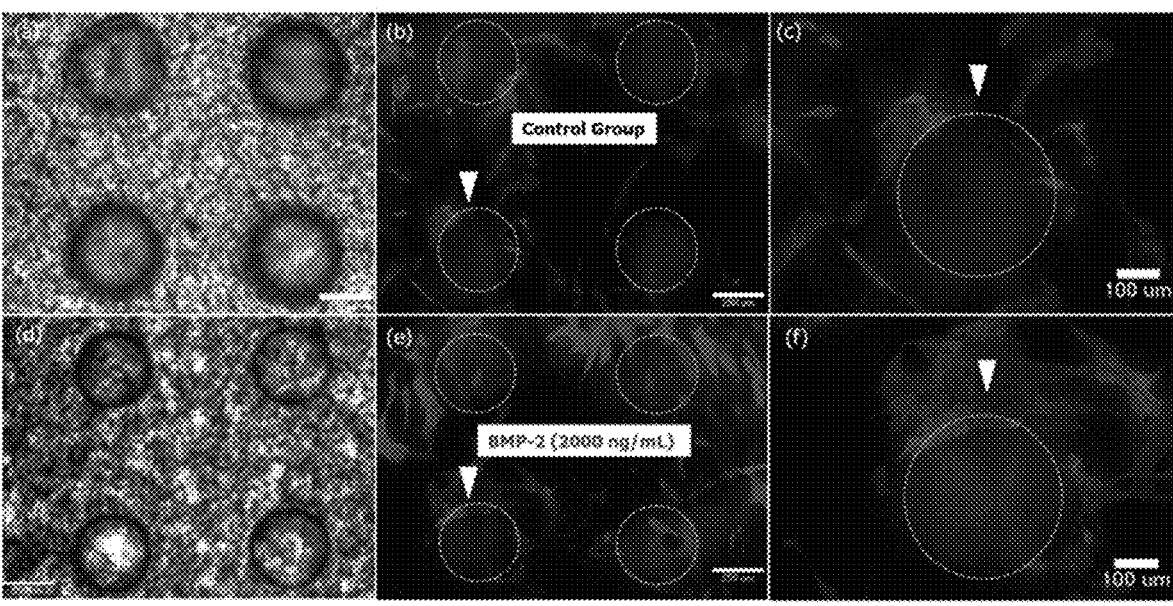
FIG. 10 illustrates actin filament staining of MG-63 cells after 6 days.
Figure 11:
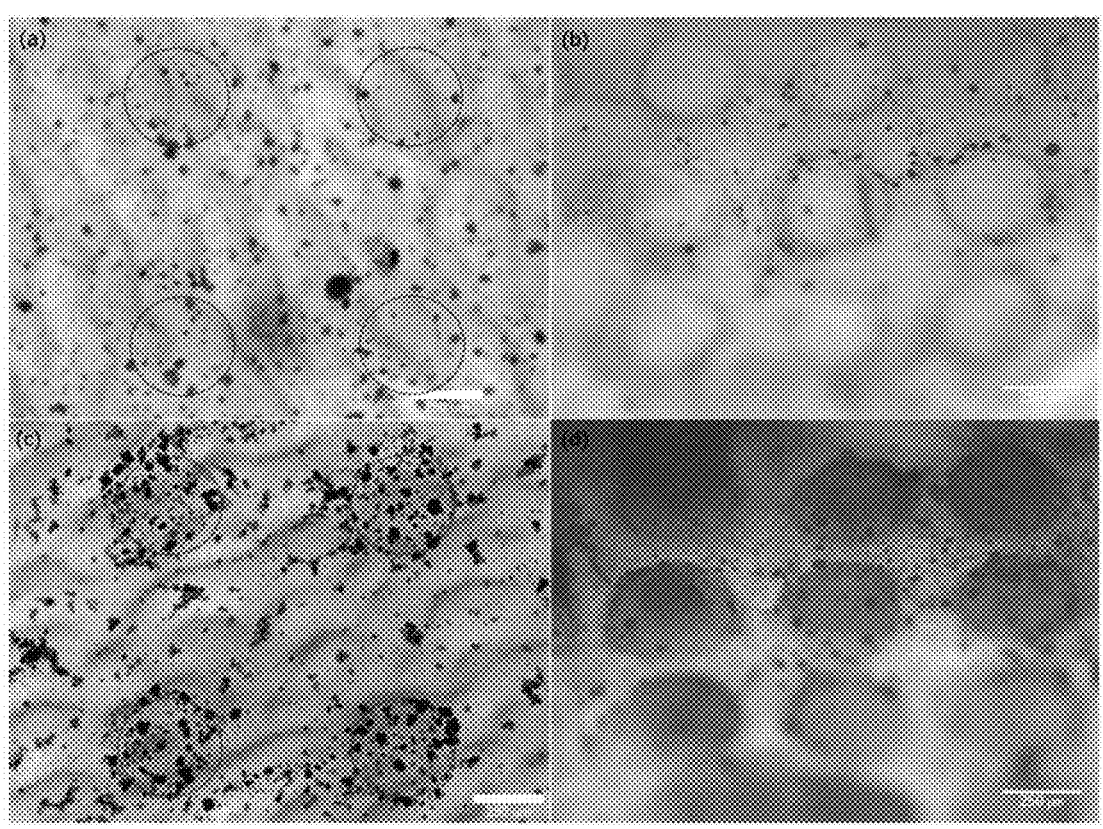
FIG. 11 illustrates osteogenic differentiation of MG-63 cells with ARS staining after 6 days.

FIGS. 10 and 11 illustrates observation of skeleton change and calcification of MG63 cells by immobilization of the bone morphogenetic protein and the local release.

FIG. 10 illustrates Actin filament staining of MG-63 cells after 6 days: (a-c) In the absence of BMP-2 and (d-f) in the presence of 2000 ng/mL BMP-2 released from the 2.5% (w/v) GelMA hydrogel micropattern on SNM.

FIG. 11 illustrates Osteogenic differentiation of MG-63 cells with ARS staining after 6 days: (a-b) In the absence of BMP-2 and (c-d) in the presence of 2000 ng/ml BMP-2 released from the 2.5% (w/v) GelMA hydrogel micropattern on SNM.

To investigate the relationship between osteogenic differentiation and BMP-2 release, MG-63 cells were cultured in the absence or presence of BMP-2 on 2.5% (w/v) GelMA hydrogel micropattern and analyzed using actin filament staining and Alizarin Red S (ARS) staining (FIG. 10). Although the SNM used as a substrate has an extracellular matrix-like surface structure, which can provide a good environment for cell attachment and proliferation, MG-63 cells were observed to adhere primarily around the GelMA pattern. In particular, when BMP-2 was immobilized, the cells were observed to grow mainly when they were attached to the pattern and were in the vicinity of the pattern. When the cytoskeleton of the cells was observed using actin filament staining, we observed that a relatively rich and dense actin network was formed between MG-63 cells in the presence of BMP-2. In addition, in the absence of BMP-2 in the GelMA pattern, the cells tended to be located around the pattern in random direction (FIG. 10 (*a*), (*b*), (*c*)); however, in the case of BMP-2 immobilization, the cells were oriented toward the central axis of each pattern (FIG. 10 (*d*), (*e*), (*f*)). In terms of osteogenic differentiation, ARS staining was used to colorimetrically distinguish the extent of calcium deposition as a result of osteoblastic differentiation. Generally, the amount of calcium in the medium increases when MG-63 cells induce bone differentiation, and the calcium ion forms a strong covalent bond with oxygen or hydroxyl group in ARS, resulting in an orange-red precipitate. Six days after seeding the MG-63 cells, calcium deposited nodules were observed under both conditions. However, as shown in FIG. 11, the calcium deposits formed by MG-63 cells on the surface of GelMA were significantly higher in the presence of BMP-2 (FIG. 11 (*c*), (*d*)) than in the control group (FIG. 11 (*a*), (*b*)). For quantitative analysis, the area of calcium deposition was calculated using the Image J software. In the BMP-2 group, the average deposition area was approximately 32 mm$^2$, whereas it was approximately 86 mm$^2$ in the control group. These results show that BMP-2 was locally released from the GelMA micropattern, which significantly affected the osteogenic differentiation of MG-63 cells. The calcium deposition correlated with the changes in the cytoskeleton after the release of BMP-2 (FIG. 10). Despite these meaningful results, the clinical application of the BMP-2 carrier is limited due to the short duration of 6 days and the in-vitro condition based on cell culture medium. Therefore, further studies such as in vivo testing and alkaline phosphatase activity (ALP) assay are still needed.

CONCLUSION

In the clinical procedure of bone grafting on a defective site, a polymer-based barrier membrane is used to prevent invasion of connective tissue into the bone regeneration area. However, although growth factors are used to promote bone formation, their use has been limited owing to problems such as burst release and action at the ectopic site depending on the growth factor carrier. By optimizing the concentrations of BMP-2 and GelMA hydrogels for immobilization and micropatterning, respectively, we demonstrate that BMP-2 is easily immobilized into micropatterned GelMA hydrogels and that the local release of BMP-2 is effectively controlled. The GelMA hydrogels provide an environment in which BMP-2 can be homogeneously laden, while the SNM supported transmission of UV light, allowing the GelMA hydrogels containing BMP-2 to crosslink rapidly on the SNM surface. The behavior of MG-63 cells in bone differentiation medium depended on the distribution of BMP-2, indicating that bone differentiation of MG-63 cells can be manipulated by controlling the immobilized BMP-2 in the GelMA hydrogel micropattern. The proposed method can be applied to various clinical treatments requiring controlled delivery of growth factors and cells, such as in bone regeneration, where the pattern size and concentration of BMP-2 can be changed depending on the size of the bone defect or the type of bone graft.

Local Release of Anticancer Drug Using Patterning Hydrogel to Nanoporous Membrane Materials and Methods Three-Dimensional (3D) Printing-Based Master Micromold The master mold, which has convex patterns to allow the construction of the hyaluronic acid (HA) hydrogel arrays, was produced using PolyJet 3D printing. Vero (RGD 824, Stratasys Ltd., MN, USA) was used as a material for the master mold in conjunction with the use of the PolyJet 3D printer (J826 prime, Stratasys Ltd.). Vero offers excellent visualization with a tensile strength in the range of 60-70 MPa, a flexural strength in the range of 75-110 MPa, and a heat deflection temperature in the range of 45-50° C. The Vero-based convex pattern on the master mold surface was designed as a hemisphere with a diameter of 700 µm, and the stacked layer thickness was set at 14 µm. After the printing of the master mold, PDMS (Dow Corning, MI, USA) the Si-based organic polymer with excellent optical transparency and mechanical properties was used to replicate the concave patterns from the convex patterns on the Vero-master mold. The PDMS solution was prepared by mixing the base polymer and the curing agent at the ratio of 10:1.5 wt %. The mixed PDMS solution was maintained in a vacuum chamber for 1 h to eliminate bubbles and was essary components, the solution was then dialyzed with DI water for at least 48 h using a dialysis bag (Molecular weight cutoffs: 12-14 kDa, Spectrum Laboratories, Piscataway, NJ, USA). After dialysis, the solution was lyophilized using a freeze dryer (TFD, IlshinBioBase, Korea) at −68° C. and 660 Pa for 4 days and was stored in a deep freezer at −70° C. in powder state for future use. The synthesized HAMA hydrogel was verified using a FT-IR Spectrometer (IN10/iS50, Thermo Scientific, MA, USA).

Fabrication of Amphipathic Membrane

To produce the amphipathic membrane, a membrane with hydrophobic and hydrophilic surfaces was electrospun sequentially. First, the solution for hydrophobic fiber was prepared to dissolve 15% (w/v) of PU (Dow Chemical, MI, USA) in a solvent of N,N dimethylformamide (DMF) (Junsei, Japan) and tetrahydrofuran (THF) (Daejung, Korea) (1:1.5 (v/v)). Subsequently, the solution for hydrophilic fiber was obtained by dissolving PU and Pluronic® F-127 (Poloxamer 407) (Sigma-Aldrich) to a concentration of 10% (w/v) and 10% (w/v) of solvent. Each mixture was stirred at 65° C. for 24 h until all the solutes were dissolved. To introduce double-faced properties on both sides, the PU membrane was synthesized first by electrospinning, and the PU-PF membrane was electrospun on top of it. For electrospinning, 10 ml of the PU solution was prepared in a 10 ml syringe with the use of a metal spinneret needle of 23 G; this aliquot was then electrospun at a flow rate of 0.4 ml/h at an applied voltage set at 13.5 kV. After electrospinning the PU membrane, 5 ml of PU-PF solution was loaded and electrospun at the same conditions as PU. The metal-based collector was located 40 cm away from the spinneret needle and was rotated at 10 revolutions per minute for 60 h. The conditions of electrospinning are summarized in Table 2. The electrospun amphipathic membrane was dried in an oven at 60° C. for 4 h, and was exposed to UV light for 10 h to sterilize it.

TABLE 2

|  | PU memebrane | PU-PF membrane |
| --- | --- | --- |
| Polymer | Polyurethane (PU) | Polyurethane (PU)/Pluronic F-127 |
| Solvent | Dimethylformamide: | Dimethylformamide: |
|  | Tetrahydrofuran = 1:1.5 (v/v) | Tetrahydrofuran = 1:1.5 (v/v) |
| Concentration | 10% (w/v) | PU = 10% (w/v)/ |
|  |  | PU-PF =: 10% (w/v) |
| Total volume | 10 mL | 5 mL |
| Voltage | 13.5 kV | 13.5 kV |
| Tip to Collector distance | 40 cm | 40 cm |
| Flow rate | 0.4 mL/h | 0.4 mL/h |
| Needle gauge | 23 G | 23 G | poured on the Vero-master mold. To prevent thermal deformation, the Vero-master mold and PDMS solution were cured at 43° C. for 24 h. After detaching the Vero-master mold, the replicated PDMS mold containing concave patterns for HA hydrogel arraying was obtained Synthesis of HAMA Hydrogel Hyaluronic acid (HA), a nontoxic degradation product, is one of the most suitable biomaterials, which has superior biocompatibility characteristics. To synthesize Hyaluronic acid methacrylate (HAMA) hydrogel, sodium hyaluronate (40 kDa, Lifecore, MN, USA) was dissolved in 100 mL DI water to a concentration of 1% (w/v), and 1 mL of methacrylic anhydride (MA) (Sigma-Aldrich, MO, USA) was added to the solution. The solution was adjusted to pH 8 following the slow addition of an aqueous solution of 5 N NaOH (Sigma-Aldrich), and continued to synthesis at 7° C. for 24 h to preserve reaction temperature. To remove unnec- Characterization of Amphipathic Membrane A high-resolution scanning electron microscope (HR-SEM) (AXIO, Zeiss, Germany) was employed to observe the surface morphology and thickness of the amphipathic membrane. The amphipathic membrane was prepared at a size of 10 mm (width)×10 mm (depth)×150 µm (height) for HR-SEM, and the PU and PU-PF surfaces were then imaged. To examine the wettability of each surface, the contact angle was measured using a contact angle meter (GSS, SurfaceTech, Korea). The amphipathic membrane was prepared on a flat holder and set to be perpendicular to the 27 G needle. Subsequently, single DI water droplets were released from a 3 mL syringe on the PU or PU-PF surfaces. The absorptiveness and dispersive influence tests were conducted using watercolor ink (red) and fluorescent bead solutions. The fluorescent bead solution was made by mixing 1000 µL of DI water and 10 µL of red fluorescent beads (10 μm) (Micromod, Germany). Subsequently, the amphipathic membrane, trimmed to 20 mm×90 mm, was folded, and was attached to the slide glass (Marienfeld Superior, Germany); the PU surface was located at the top and the PU-PF surface at the bottom, with both surfaces facing upward, and vice versa. These prepared samples were tilted at 45°, and 300 L of watercolor ink (red) or bead solution was dropped on the top of each sample. The adsorbed or permeated area was observed by using the HR-SEM and fluorescent microscopy (Zeiss) according to PU or PU-PF surfaces. The size of images was then converted to 0.651 pixels/μm ratio, and trapped beads area was quantitatively analyzed and measured using Image J software (National Institutes of Health, Bethesda, MD, USA).

HAMA Hydrogel Arraying on Amphipathic Membrane

The HAMA hydrogel arrays were formed by photocross-linking the amphipathic membrane and replicated PDMS mold. After sterilization with autoclaving, the surfaces of the PDMS concave mold and amphipathic membrane were treated with oxygen plasma at 60 W (Cute, Femto-Science, Korea) for 30 s to facilitate filling with HAMA solution. Prelyophilized HAMA and 0.05% (w/v) 2-hydroxy-4'-(2-hydroxyethxy)-2-methylpropiophenone (TCI, Japan) were dissolved in Dulbecco's phosphate-buffered saline (DPBS) (Welgene, Korea) to form the HAMA solution. The HAMA solution was applied to a concave PDMS mold and scratched to fill the inner parts of the pattern, and the residual solution was removed. The amphipathic membrane (15 mm×15 mm) was then used to cover the HAMA-filled concave pattern; the hydrophilic side of the amphipathic membrane and pattern side of the PDMS mold faced each other. To achieve the photo-crosslinking of the HAMA solution on the amphipathic membrane, the HAMA-filled PDMS mold was exposed to UV light (Omnicure S2000, Excelias Techonolhies Corp., MA, USA) (wavelength: 360 nm, intensity: 10000 mW/cm$^2$) at 8 cm for 50 s. Detachment of the PDMS mold from the amphipathic membrane successfully led to the photo-crosslinking of the HAMA hydrogel arrays on the amphipathic membrane. To confirm the HAMA hydrogel arraying, the 10 μm fluorescent beads were added to the HAMA solution to observe the array formation using fluorescent microscopy.

Diffusion Test on Amphipathic Membrane

To study the diffusion profile from the immobilized substance HAMA hydrogel arrays on the amphipathic membrane. Briefly, FITC-BSA was encapsulated in 2.5% (w/v) or 5% (w/v) solutions, and was refreshed with 2 mL of DI water daily for 6 days. Each time the DI water was refreshed, the fluorescence intensities of the same spots on all HAMA hydrogel arrays on the amphipathic membrane were recorded. To investigate the role of the amphipathic membrane for mass transport as a substrate at different wettability values, a 3D environment was emulated using a lab-made rectangular acrylic cube with a size of 25 mm (width)×20 mm (depth)×30 mm (height). The assembled acrylic cube was filled with DI water through its opened upper side. The watercolor ink (blue) was mixed in the HAMA hydrogel arrays, immobilized on the amphipathic membrane, and was placed on the top of the acrylic cube toward the inner parts of DI water, or in the opposite direction. The diffusing profile of the HAMA hydrogel was observed and tracked with a digital camera (Canon, Japan). The approximation equation for diffusion time can be followed:

$$t \approx \frac{x^2}{2D}$$

where D denotes the diffusion coefficient of an ink, x the mean distance traveled by the diffusing, and t the elapsed time since diffusion began.

5-FU Immobilization and Release with YD-10B Cells

To estimate the rate of apoptosis of tumor cells at a controlled release anticancer drug rate, YD-10B cells derived from human oral squamous cancer were cultured on a 15% (w/v) HAMA hydrogel-arrayed amphipathic membrane. The amphipathic membrane was prepared at a size of 20 mm×20 mm and was fixed at the bottom of the cell culture dish with the use of PDMS blocks as supporters to prevent floating in the culture media. Overall, YD-10B cells (100 μL, cell density of 1.0×106 cells/mL) were seeded on the HAMA hydrogel-arrayed amphipathic membrane that contained 5-FU. As a control group, YD-10B cells without 5-FU were seeded on the array. The cells were cultured in culture media [RPMI (RPMI 1640 medium, HEPES)] (Gibco, CA, USA) with 10% fetal bovine serum (FBS) (Gibco) and 1% penicillin/streptomycin (Gibco) in an incubator (MCO-18AIC, Sanyo, Japan) at 5% $CO_2$ and 37.5° C. After 5 days, the live/dead assay [live/dead viability/cytotoxicity kit (Invitrogen, MA, USA)] was conducted to evaluate anticancer performance. The solution for the live/dead assay was mixed with 20 μL of Ethidium Homodimer-1 (EthD-1) and 5 μL of calcein-AM in 10 mL of DPBS in the dark room. The culture media were eliminated using a micropipette, and the residual media were washed twice by DPBS. The staining solution was added on the arrayed amphipathic membrane and incubated for 40 min. The viability of the YD-10B cells on the amphipathic membrane was evaluated by a fluorescent microscope (Zeiss, Germany). The cytoplasm of live cells was stained with calcein-AM (green fluorescence, excitation wavelength: 488 nm/emission wavelength: 515 nm), while the DNA of dead cells was stained with EthD-1 as fluorescence red (excitation: 570 nm/emission: 602 nm). Additionally, the actin filaments of cells were stained to verify the colony formations of tumor cells. For the fixation of cultured cells, the membrane was washed with DPBS and was immersed in 4% paraformaldehyde (PFA) for 15 min. Triton X-100 was used for permeabilization for 5 min at −20° C. on a PFA-immersed membrane. After washing the Triton X-100, the membrane was immersed in 1% BSA for 45 min at 27.5° C. The cells on the membrane were stained with Alexa Fluor 568 phalloidin (Invitrogen) for 2 h. The stained actin filaments were observed to fluoresce in red when the Texas red filter was used in a fluorescent microscope.

Results

Bilayer Amphipathic Membrane

Figure 12:
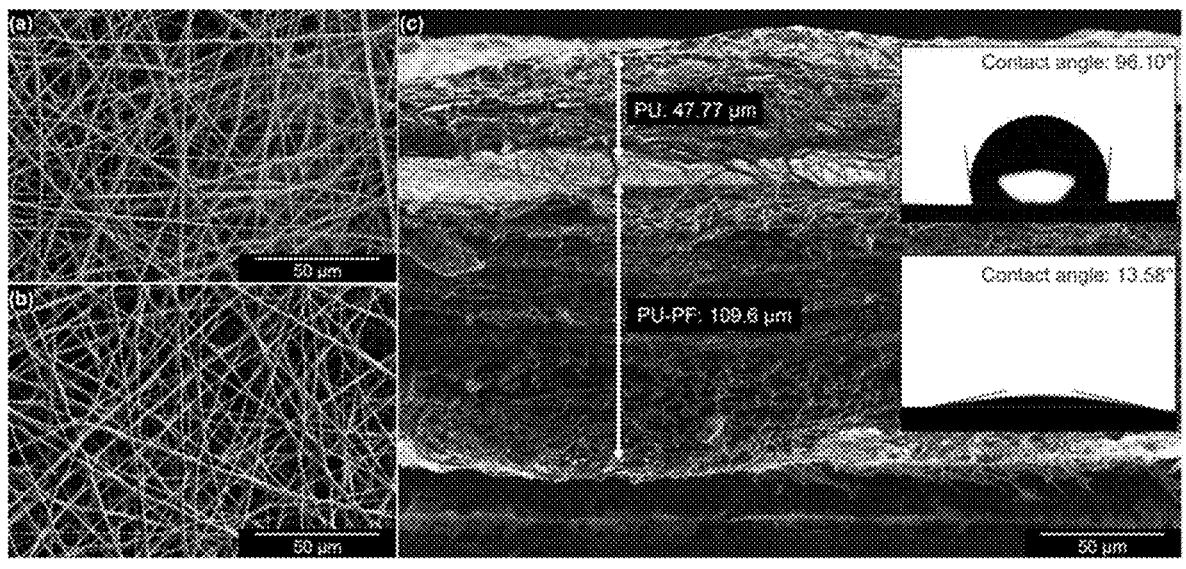
FIG. 12 illustrates scanning electron microscopy (SEM) images.

The electrospinning-based bilayer amphipathic membrane is shown in FIG. 12. Both the Polyurethane (PU) and the PU-Pluronic® F-127 (Poloxamer 407) surfaces of the membrane have well defined straight fibers that are randomly stacked and form numerous pores (FIG. 12 (a), (b)). The cross-section of the bilayer membrane is shown in FIG. 112 (c); the thickness of PU and PU-PF layer are measured to be equal to 50 μm and 110 μm, respectively. As shown in FIG. 12 (c), different surfaces had different wettability values. The measured contact angle on the hydrophobic surface was 96.1°; conversely, on the hydrophilic surface, the contact angle was 13.58°. We assumed the properties of Pluronic® F-127 (Poloxamer 407) with the hydrophilic polyethylene glycol chains reported previously.

Figure 13:
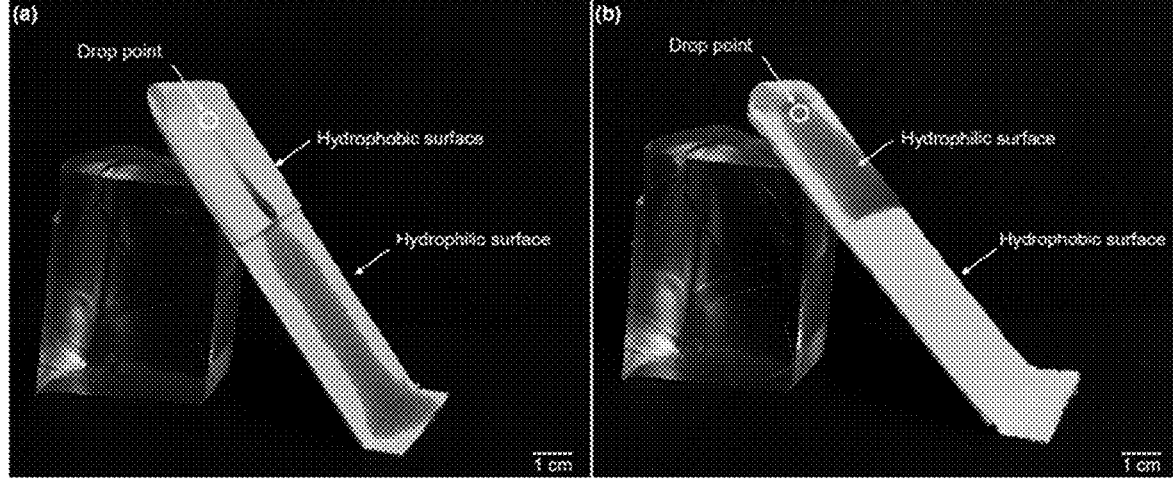
FIG. 13 illustrates hydrophilicity of amphipathic membrane.
Figure 14:
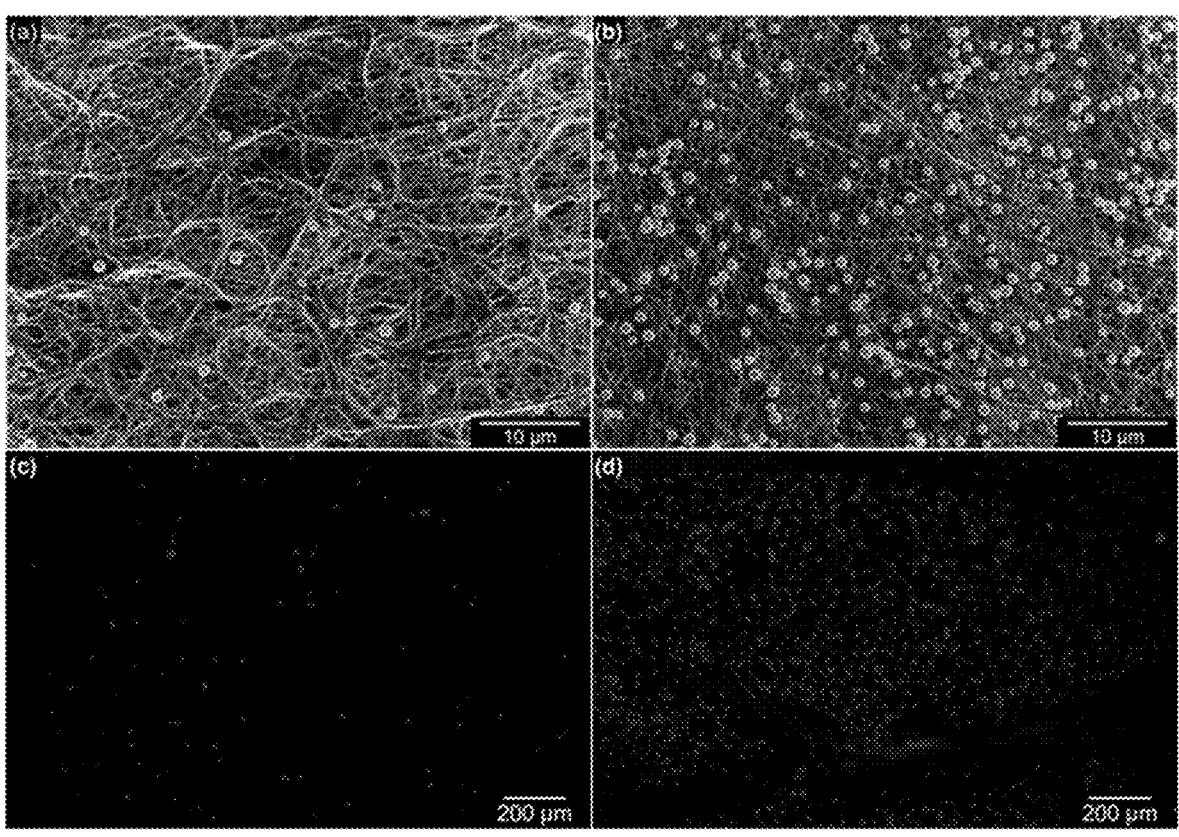
FIG. 14 illustrates SEM and fluorescence microphotograghs of residual beads on PU and PU-PF surfaces of amphipathic membrane after the addition of fluorescent bead solution.

These properties of the amphipathic membrane were quantified by the absorptiveness and dispersive influence tests (FIG. 13). When the hydrophobic PU surface was located at the top, watercolor ink (red) was not absorbed, but flowed along the slope, and was absorbed into the hydrophilic PU-PF surface at the bottom (FIG. 13 (*a*)). Conversely, watercolor ink (red) was rapidly absorbed and did not flow to the bottom when the hydrophilic PU-PF surface was located at the top (FIG. 13 (*b*)). In addition, a solution that contained fluorescent beads was dropped on both surfaces of the membrane to observe the number of beads left (FIG. 14). The two types of folded membrane were tilted by 45°, and the bead solution was dropped at the same position to compare the number of residual beads on the membrane. The number of residual beads on the PU-PF surface outnumbered that on the hydrophobic PU surface as the solution was absorbed in the hydrophilic PU-PF surface (FIG. 14 (*a*), (*b*)). In the quantitative analysis of the trapped beads within areas equal to 2.3 mm2, these occupied an area of 0.017 mm2 on the hydrophobic surface and 0.265 mm2 on the hydrophilic surface (FIG. 14 (*c*), (*d*)). The area of the bead trapped on the hydrophilic surface was calculated to be 3.7 times higher than those on the hydrophobic surface. The surface energy, which determines the wettability of amphipathic membranes, was evaluated by the contact angle, absorptiveness, and dispersive influence tests. In the PU, only the electrospun surface was tested, and the measured contact angle was high because the PU had low-surface energy and the dropped deionized (DI) water had high surface tension. However, the contact angle was lowered by the increased surface energy due to the hydrophilic polar group, which was introduced on the surface by F-127. In this regard, it can also be explained why the injected fluorescent beads were absorbed together with the solution on the hydrophilic surface. These results indicate the successful physical properties of the membrane that can selectively permeate or repel materials owing to the wettability of individual surfaces. In qualitative analyses, the spectra of both sides of the membrane obtained with the use of the Fourier Transform Infrared (FT-IR) spectrophotometer are obtained. The FT-IR spectra for both the PU and PU-PF membranes were confirmed with those in previously published reports. The spectra show that the PU membrane spectrum had sharp bends at 1728 and 1701 cm$^{-1}$, which were assigned to C=O stretching. The peaks at 3325 and 1103 cm$^{-1}$ were related to —NH group and C—O—C stretching, respectively. In the PU-PF spectra, the C=O 1728-1701 cm$^{-1}$ peaks were attributed to the PU membrane. However, according to the overlapped —CH2 (SP2) peaks at 2854-2939 cm$^{-}$1, and —CH2 (SP3) at 1342 cm$^{-1}$, the —OH group broadly overlapped at the N—H group (3325 cm$^{-1}$). Therefore, the peak at 1102 cm$^{-1}$ for the PU-PF side was approximately 1.5 times higher, and may have been derived from the C—O—C bond of Pluronic® F-127 (Poloxamer 407) used for hydrophilization.

HAMA Hydrogel Array

Figure 15:
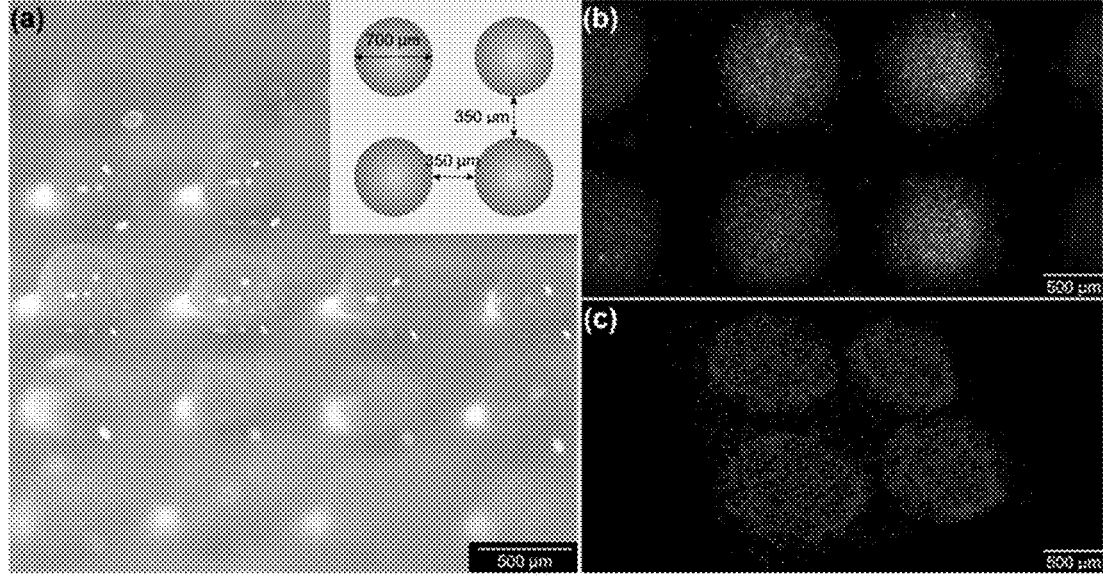
FIG. 15 illustrates HA-based hydrogel array on hydrophilic surface of amphipathic membrane.

The crosslinked HAMA hydrogel arrays on the hydrophilic surface of the amphipathic membrane, based on the use of a 15% (w/v) HAMA solution, are shown in FIG. 15. In this process, ultraviolet (UV) light must reach the HAMA solution on the prepared amphipathic membrane through the transparent PDMS mold. Additionally, the crosslinked HAMA hydrogel should be separated from the PDMS mold while maintaining attachment with the amphipathic membrane. On the hydrophilic PU-PF surface, the HAMA solution was rapidly absorbed into the amphipathic membrane and was crosslinked with a high adherence so that it could be easily separated from the PDMS mold. For this reason, the integrated hydrogel array has a hemispherical shape with a diameter equal to 700 μm, the same size as the designed and manufactured PDMS mold (FIG. 15 (*a*)). Therefore, the mixed fluorescent beads were observed only in the crosslinked HAMA hydrogel arrays and not in other parts of the amphipathic membrane, as shown in FIG. 15 (*b*), (*c*). Specifically, the lyophilized HAMA hydrogel was confirmed by using the FT-IR spectra. The main functional groups of synthesized HAMA were identified in previous research studies. Briefly, The FT-IR spectrum shows an intense signal at 3277 cm$^{-1}$ assigned to the N—H or O—H stretching vibrations. These broad peaks are assigned to the presence of alcohols-phenols, amines amides, and carboxylic acids. The moderate peak at 2890 cm$^{-1}$ may be due to the C—H stretching of alkyl chain, and indicates the presence of aromatic C—H bonds observed in the 3200 to 3000 cm$^{-1}$ regions; these can be overlapped by broad N—H and O—H peaks. Additionally, the SP3 C—H peaks at 1405 and 1376 cm$^{-1}$ (methyl and methylene group) and vibrations of alkoxy C—O bonds in ether, phenol, and alcohol at 1028 cm$^{-1}$ support the presence of hydrophilic functional groups, such as O—H or —COOH. Therefore, we believe that these hydrophilic functional groups (—OH, —COOH, and —NH) of the PU-PF membrane and HAMA hydrogel can precisely control the hemispherical arraying for drug delivery. Furthermore, it is suggested that the proposed process can easily and successfully inject and control the target materials within the HAMA hydrogel arrays.

Diffusion Aspects

Figure 16:
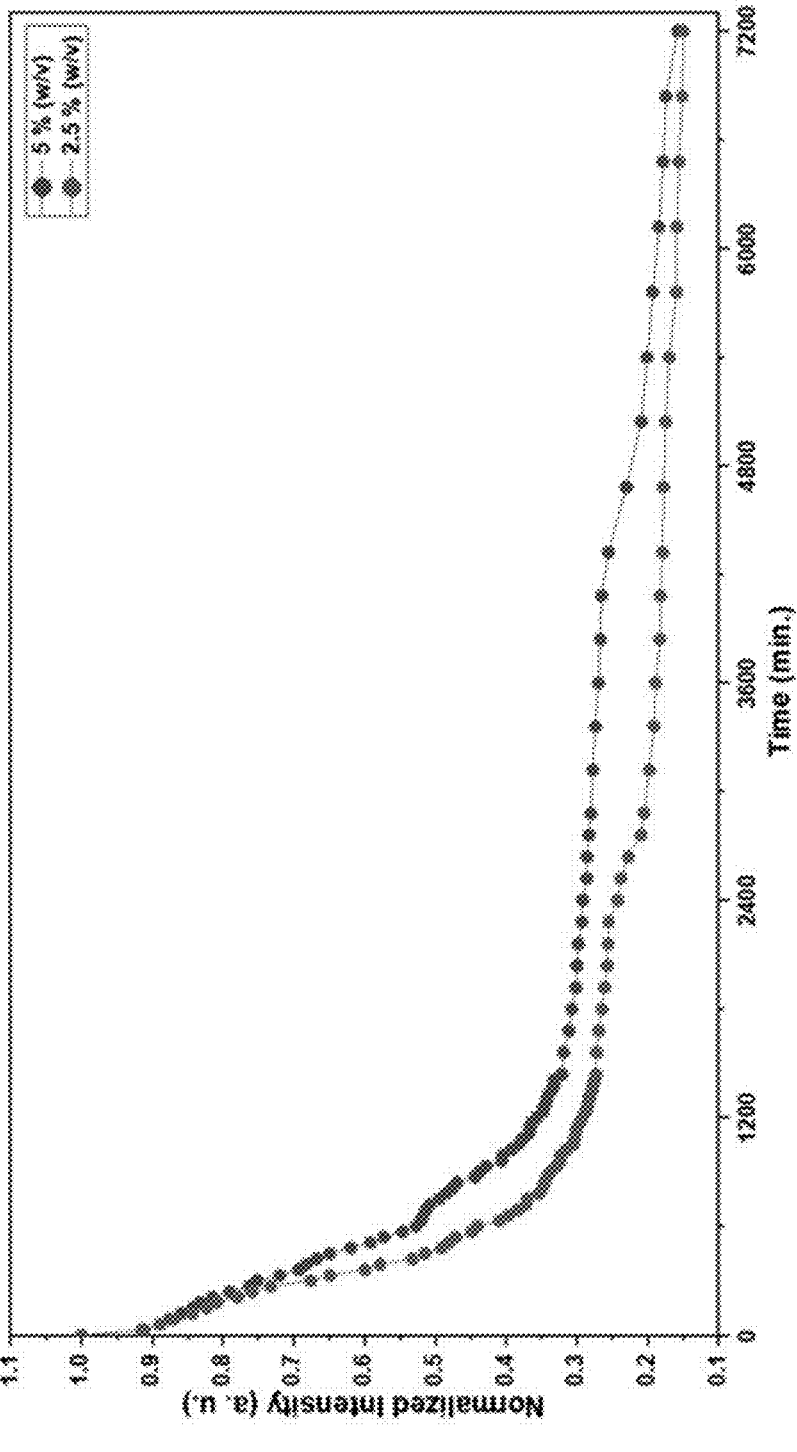
FIG. 16 illustrates release profiles of the FITC-BSA according to HA hydrogel concentration. FITC-BSA release behaviors of 2.5% (w/v) and 5% (w/v) of HA-based hydrogel for 5 days.
Figure 17:
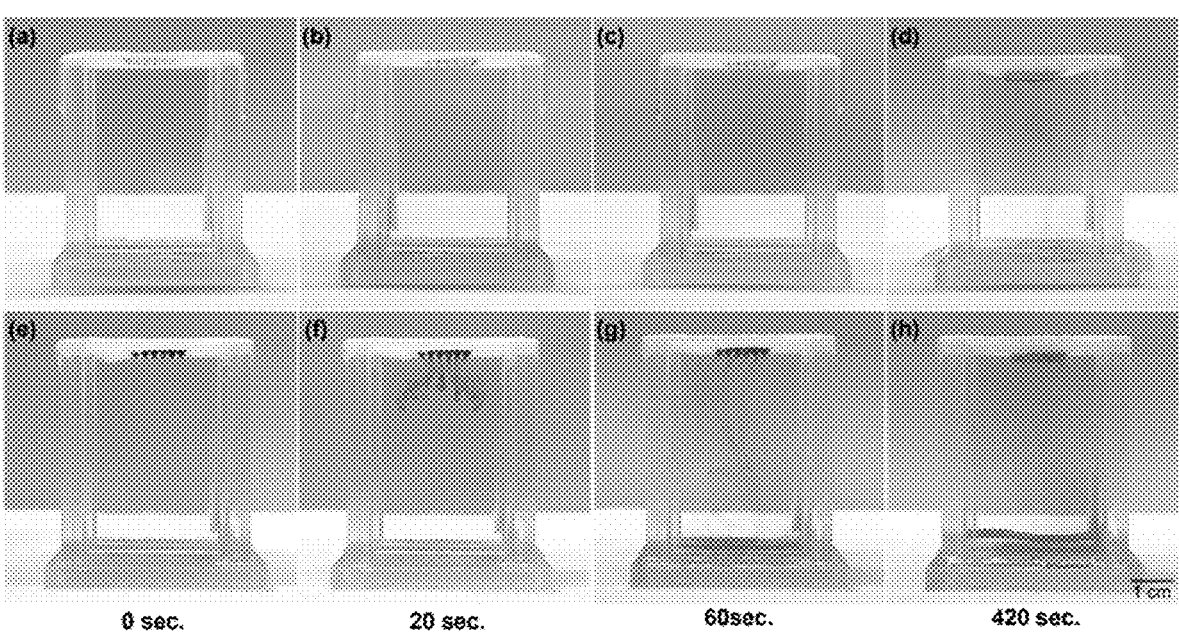
FIG. 17 illustrates a role of amphipathic membrane for mass transport as a substrate at different wettability values.

To demonstrate the encapsulation and release potential of materials based on HAMA hydrogel arrays, fluorescein isothiocyanate labelled bovine serum albumin (FITC-BSA) was added to the HAMA solution and crosslinked to amphipathic membranes in arrays. At the HAMA concentration of 5% (w/v) or higher, the shape was not intact owing to the high viscosity when the array was separated from the PDMS mold. Thus, the employed test was conducted with only 2.5% (w/v) and 5% (w/v) of HAMA hydrogel. FIG. 16 shows the intensity profile of the fluorescence intensity change of the HAMA hydrogel over time after the fluorescence intensity value inside the pattern was specified to be 1.00 based on the first measured intensity value after the formation of the array. The relative fluorescence intensity values of the arrays after 10 h in both conditions were reduced to approximately 0.44 and 0.53 in 2.5% (w/v) and 5% (w/v) HAMA, respectively. The calculated release rate was approximately 1.5 times higher in the 2.5% (w/v) compared with the 5% (w/v) HAMA hydrogel. On day 5, the FITC-BSA released from the HAMA hydrogels became similar, and the measured fluorescence intensity values were 0.15 and 0.16 in the cases of the 2.5% (w/v) and 5% (w/v) HAMA hydrogel concentrations, respectively. This means that the release control of the target substance with the same concentration can be controlled by the concentration and array of the HAMA hydrogel. In terms of the role of the amphipathic membrane (which possesses both hydrophobic and hydrophilic features), a 3D environment was constructed, and the diffusion phenomenon of the immobilized material was observed differently depending on the wettability. Given that the hydrophobic surface of the electrospun membrane could not be arrayed owing to the low-surface tension of the membrane, only the hydrophilic surface was arrayed by mixing the same concentration of watercolor ink (blue) and HAMA hydrogel. As shown in FIG. 17 (*a*)-(*d*), when the unpattern hydrophobic surface inside the water-filled cube was in contact with water in a static state, the watercolor ink slowly diffused toward the water after approximately 5 min from the HAMA hydrogel array. The diffusion coefficient values measured under each condition were 0.00286 cm$^2$/s for the hydrophobic surface and 0.02500 cm$^2$/s for the hydrophilic surface, which was approximately 8.74 times higher in the hydrophilic surface. In addition, it was observed that the hydrophobic membrane was pulled owing to the influence of the surface tension of the filled water. In contrast, as shown in FIG. 17 (*e*)-(*h*), when a membrane arrayed on a hydrophilic surface contacted water, the watercolor ink diffused into the water at a high rate throughout the HAMA hydrogel arrays. Owing to the high-surface tension of the membrane on the hydrophilic surface in contact with water, the membrane was not contacted by water, and could maintain its original shape. These results demonstrate that the hydrophobic surface of amphipathic membrane acts to inhibit or impede the passage and transportation of substances, whereas the hydrophilic surface can facilitate both the immobilization and transportation of substances.

Apoptosis of YD-10B Cells with 5-FU Release

Figure 18:
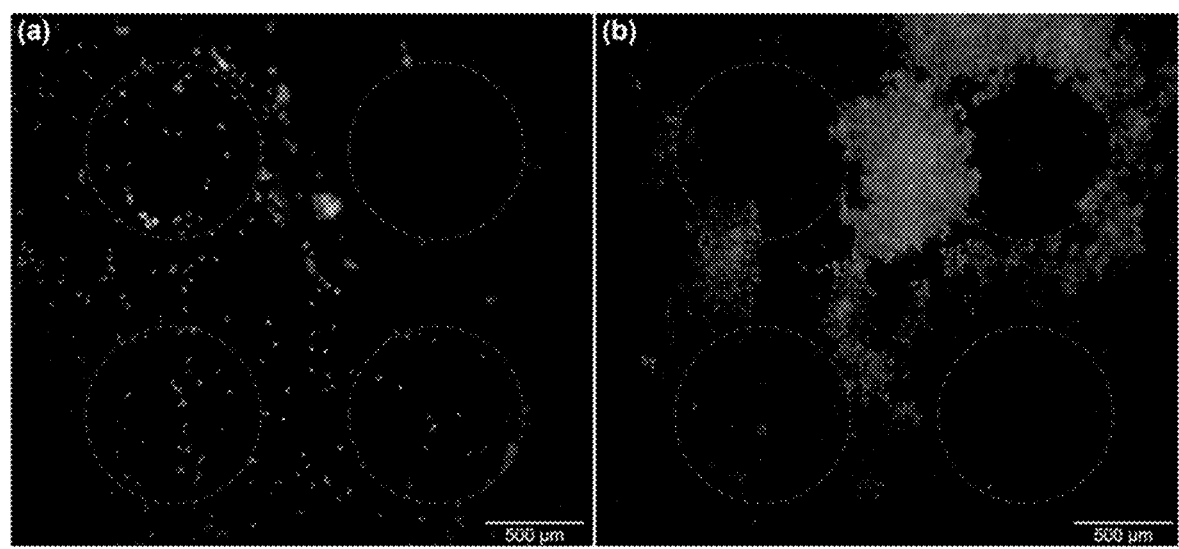
FIG. 18 illustrates Live/Dead assay of YD-10B cultured on HA hydrogel arrays for 5 days.
Figure 19:
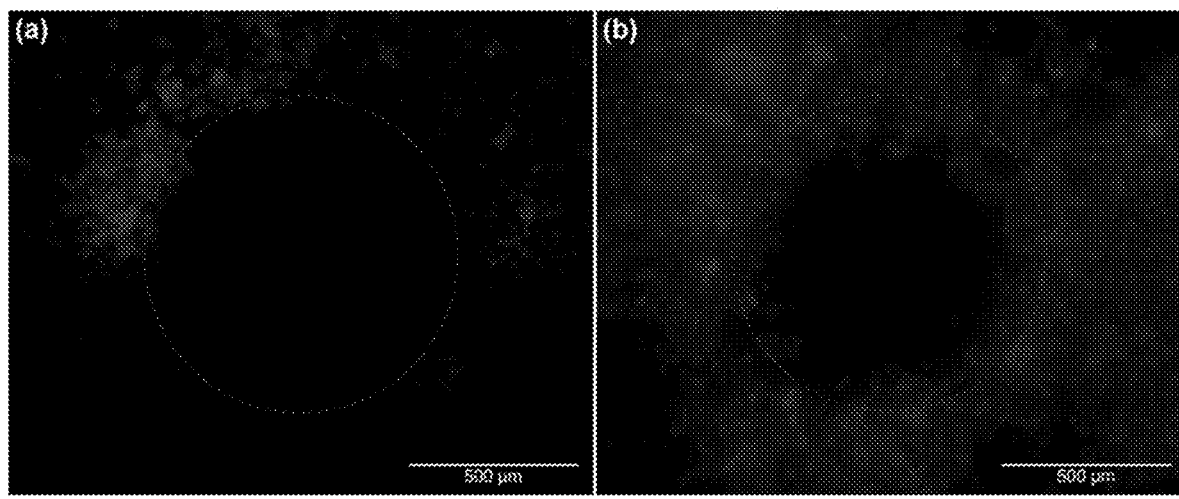
FIG. 19 illustrates the difference in cell growth according to anticancer encapsulation by staining the fibers of YD-10B cells cultured in an array.

The human oral squamous cell carcinoma YD-10B cells were seeded on HAMA-based hydrogel arrays encapsulated with 5-FU and on arrays that did not contain anything, and were then cultured for 5 days. The cellular response following the addition of 5-FU (known as an anticancer drug) in the HAMA hydrogel on the surface of the hydrophilic PU-PF was observed. Cell cultures wherein 5-FU was not added (but all other conditions were the same as the test cultures) served as controls. As a result of the viability of cells based on the live/dead assay, fluorescent, red-expressed dead cells and fluorescent, green-expressed living cells were identified in both cases. As a result of the previous test with the use of the watercolor ink, it could be estimated that the cells of the experimental group in which 5-FU was present were already dead cells before they were attached and proliferated on the amphipathic membrane owing to the initial release of a large amount of 5-FU. When cultured in HAMA hydrogel arrays containing 5-FU, only a few viable cells were visible (FIG. 18 (*a*)), whereas when 5-FU was omitted, numerous cells aggregated and grew around the arrays (FIG. 18 (*b*)). In both conditions, for comparison of adherent and viable cells, the adhesion rate was reduced by approximately 48% when 5-FU was encapsulated in HAMA hydrogel as a result of calculation based on the expression area after green-fluorescent calcein acetoxymethyl (calcein-AM) staining. The measured adhesion area cultured with 5-FU was approximately 19,321 μm$^2$, and approximately 914,734 μm$^2$ without 5-FU. FIG. 19 shows the difference in cell growth according to anticancer encapsulation by staining the fibers of YD-10B cells cultured in an array. Based on the observation that YD-10B cells grow in clusters, YD-10B cells grew while they formed relatively larger and cohesive colonies only when 5-FU was omitted. These results suggest that 5-FU can be mixed with HAMA hydrogel to array, and 5-FU encapsulated in the array can inhibit the growth and proliferation of cells during the cell culture process.

CONCLUSION

In this study, sustained release of the drug attached to a specific site was achieved using biocompatible hydrogel and amphipathic membrane to prevent the side effects of the initial drug burst. Hyaluronic acid (HA) and methacrylic anhydride (MA) were used to synthesize the hydrogel, which was used as a carrier to protect and deliver the drug, and the solution with the 5-FU drug was crosslinked to load the drug in a 3D mesh structure; the latter consisted of hydrophilic fibers exposed to UV light. The HAMA-array was designed for localized 5-FU drug release while the surface area was increased. A semipermeable membrane was used as a patch to attach a drug containing hydrogel array to the surface of the target body. To fix the arrays (which acted as the hydrogel carriers), they were set on the hydrophilic membrane surface, and the hydrophobic surface was directed to the outer part of the attached surface to prevent the inflow of impurities from the outer environment using the characteristics of the amphipathic membrane. Tumor cells were seeded on the HAMA hydrogel array loaded with an anticancer and was cultured for 5 days to confirm that the YD-10B cells did not proliferate as documented by the live/dead assay and actin staining; the cells aggregated and proliferated when the anticancer drug was not used. In this study, we propose the use of the HAMA-based hydrogel arrays for controlled release of drugs in tissue regeneration and chemotherapy.

Due to the development of the delivery method capable of controlling local release of a bone morphogenetic protein and anticancer drug through a hydrogel on an electrospun nanoporous membrane used in the present invention and the manufacturing method thereof, it is possible to simultaneously realize localized and quantitative release of the bone morphogenetic protein for bone regeneration and the anticancer drug for cancer degradation and the effect of membrane to prevent the infiltration of connective tissue used in existing clinic fields, it is expected that new applications to the existing clinic and a rapid entry into the market can be achieved.

Fundamental technologies and products having both local delivery and release functions of membranes, such as bone morphogenetic proteins and anticancer drugs, have not yet been disclosed in the world. Therefore, it is essential to secure the fundamental technologies.

In addition, the fundamental technology disclosed in the present invention has not yet been reported in industrial fields. Above all, the local delivery of the bone morphogenetic protein and the anticancer drug by hydrogel and the effect of the membrane that can prevent the infiltration of connective tissue can be achieved simultaneously. Therefore, in the fields such as orthopedics, dentistry, dermatology and cancer therapy, the possibility of transferring technology to medical companies and pharmaceutical companies is very high.

What is claimed is:

1. A method of controlling local release of target compounds containing a bone morphogenetic protein or anticancer drug by patterning a hydrogel onto an electrospun nanoporous membrane, wherein the patterning of the hydrogel onto the electrospun nanoporous membrane includes:

(S1) preparing a micromold with a plurality of concave grooves;

(S2) pouring a hydrogel solution comprising the target compounds into the micromold;

(S3) filling the plurality of concave grooves on the micromold with the hydrogel solution;

(S4) covering an electrospun nanoporous membrane on the micromold filled with the hydrogel solution, (S5) patterning a hemispherical hydrogel onto the electrospun nanoporous membrane by crosslinking the hydrogel onto the electrospun nanoporous membrane; and (S6) detaching the micromold from the hemispherical hydrogel patterned electrospun nanoporous membrane, wherein the electrospun nanoporous membrane is manufactured by an electrospinning process using polyurethane and Poloxamer 407 dissolved to a concentration of 10% (w/v) and 10% (w/v) of solvent, wherein the hemispherical hydrogel is at a concentration selected from the group consisting of 2.5% (w/v), 5% (w/v), 10% (w/v) and 15% (w/v), and wherein the hemispherical hydrogel is configured to control release of the target compounds based on the hydrogel concentration.

2. The method according to claim 1, wherein the hydrogel contains the target compounds and at least one of gelatin methacryloyl (gel-MA), hyaluronic acid, Na-alginate and hyaluronic acid methacrylate (HAMA).

3. The method according to claim 1, wherein the target compounds are at a concentration selected from 1-2000 ng/mL.

4. The method according to claim 1, wherein the electrospun nanoporous membrane has the surface wettability as the contact angle 82.89±1.3°.

5. The method according to claim 1, wherein the crosslinking is executed by exposing the hydrophilic functional groups of the hydrogel and the electrospun nanoporous membrane to a UV light at a wavelength of 360 nm and an intensity of 10,000 $mW/cm^2$, wherein the hydrophilic functional groups of the hydrogel are selected from the group consisting of —OH, —COOH, and —NH, and wherein the hemispherical hydrogel is patterned onto the electrospun nanoporous membrane.

6. A method of controlling local release of target compounds containing a bone morphogenetic protein or anticancer drug by patterning a hydrogel onto an electrospun amphipathic nanoporous membrane, wherein the patterning of the hydrogel onto the electrospun amphipathic nanoporous membrane includes:

(S1) preparing a micromold with a plurality of concave grooves;

(S2) pouring a hydrogel solution comprising the target compounds into the micromold;

(S3) filling the plurality of concave grooves on the micromold with the hydrogel solution;

(S4) covering a hydrophilic layer of electrospun amphipathic nanoporous membrane on the micromold filled with the hydrogel solution, (S5) patterning a hemispherical hydrogel onto the electrospun amphipathic nanoporous membrane by crosslinking the hydrogel onto the electrospun amphipathic nanoporous membrane; and (S6) detaching the micromold from the hemispherical hydrogel patterned electrospun amphipathic nanoporous membrane, wherein the electrospun amphipathic nanoporous membrane comprises a hydrophobic layer and a hydrophilic layer, wherein the hydrophilic layer is manufactured by an electrospinning process on the hydrophobic layer using polyurethane and Poloxamer 407 dissolved to a concentration of 10% (w/v) and 10% (w/v) of solvent, wherein the hemispherical hydrogel is at a concentration selected from the group consisting of 2.5% (w/v), 5% (w/v), 10% (w/v) and 15% (w/v), and wherein the hemispherical hydrogel is configured to control release of the target compounds based on the hydrogel concentration.

7. The method according to claim 6, wherein the hydrogel contains the target compounds and at least one of gelatin methacryloyl (gel-MA), hyaluronic acid, Na-alginate and hyaluronic acid methacrylate (HAMA).

8. The method according to claim 6, wherein the target compounds are at a concentration selected from 1-2000 ng/mL.

9. The method according to claim 6, wherein the hydrophobic layer is manufactured by an electrospinning process using polyurethane dissolved to a concentration of 10% (w/v) solvent.

10. The method according to claim 6, wherein the hydrophilic layer has the surface wettability as the contact angle 82.89±1.3°.

11. The method according to claim 6, wherein the crosslinking is executed by exposing the hydrophilic functional groups of the hydrogel and the electrospun amphipathic nanoporous membrane to a UV light at a wavelength of 360 nm and an intensity of 10,000 $mW/cm^2$, wherein the hydrophilic functional groups of the hydrogel are selected from the group consisting of —OH, —COOH, and —NH, and wherein the hemispherical hydrogel is patterned onto the hydrophilic layer of the electrospun amphipathic nanoporous membrane.

* * * * *